US010210633B2

(12) United States Patent
Yamakawa et al.

(10) Patent No.: US 10,210,633 B2
(45) Date of Patent: Feb. 19, 2019

(54) X-RAY CT DEVICE AND SEQUENTIAL CORRECTION PARAMETER DETERMINATION METHOD

(71) Applicant: Hitachi, Ltd., Chiyoda-ku, Tokyo (JP)

(72) Inventors: Keisuke Yamakawa, Tokyo (JP); Shinichi Kojima, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/580,488

(22) PCT Filed: Jun. 6, 2016

(86) PCT No.: PCT/JP2016/066753
§ 371 (c)(1),
(2) Date: Dec. 7, 2017

(87) PCT Pub. No.: WO2016/199716
PCT Pub. Date: Dec. 15, 2016

(65) Prior Publication Data
US 2018/0174335 A1   Jun. 21, 2018

(30) Foreign Application Priority Data
Jun. 12, 2015   (JP) ................................. 2015-119148

(51) Int. Cl.
*G06K 9/00* (2006.01)
*G06T 11/00* (2006.01)
(Continued)

(52) U.S. Cl.
CPC ............ *G06T 11/006* (2013.01); *A61B 6/032* (2013.01); *A61B 6/5205* (2013.01);
(Continued)

(58) Field of Classification Search
CPC . G06T 11/006; G06T 5/002; G06T 2211/424; G06T 2207/10081; A61B 6/032; A61B 6/5258; A61B 6/5205
See application file for complete search history.

(56) References Cited

U.S. PATENT DOCUMENTS

2013/0101192 A1* 4/2013 Nakanishi ............. G06T 11/006
382/131
2013/0108128 A1* 5/2013 Yu ......................... G06T 11/006
382/131
(Continued)

FOREIGN PATENT DOCUMENTS

CN   103501702 A   1/2014
CN   103619259 A   3/2014
(Continued)

OTHER PUBLICATIONS

International Preliminary Report on Patentability (PCT/IB/338 & PCT/IB/373) issued in PCT Application No. PCT/JP2016/066753 dated Dec. 21, 2017, including English translation of document C2 (Japanese-language Written Opinion (PCT/ISA/237)) previously filed on Dec. 7, 2017 (5 pages).
(Continued)

*Primary Examiner* — John Strege
(74) *Attorney, Agent, or Firm* — Crowell & Moring LLP

(57) ABSTRACT

High-quality image and low radiation exposure are achieved without increasing man-hours and data amount to be held. A table of iterative correction parameters optimized in the representative imaging conditions is held and an iterative correction parameter optimized in the actual imaging conditions is determined from the iterative correction parameters held in the table. In addition to the parameter table, a reference weight is also held and is reflected to generate the iterative correction parameter for each pixel position.

11 Claims, 19 Drawing Sheets

(51) Int. Cl.
  *A61B 6/03* (2006.01)
  *A61B 6/00* (2006.01)
  *G06T 5/00* (2006.01)
(52) U.S. Cl.
  CPC ............ *A61B 6/5258* (2013.01); *G06T 5/002* (2013.01); *G06T 2207/10081* (2013.01); *G06T 2211/424* (2013.01)

(56) References Cited

U.S. PATENT DOCUMENTS

| | | |
|---|---|---|
| 2013/0336562 A1 | 12/2013 | Zamyatin et al. |
| 2013/0343508 A1* | 12/2013 | Hagiwara ............... G06T 5/001 378/4 |
| 2014/0193055 A1* | 7/2014 | Takahashi ............ G06T 11/006 382/131 |
| 2014/0226887 A1 | 8/2014 | Takahashi et al. |
| 2016/0143606 A1* | 5/2016 | Yamakawa ............ A61B 6/032 378/19 |
| 2017/0119335 A1* | 5/2017 | Yamakawa ............ A61B 6/032 |

FOREIGN PATENT DOCUMENTS

| | | |
|---|---|---|
| JP | 2006-25868 A | 2/2006 |
| JP | 4535795 B2 | 9/2010 |
| JP | 2014-408 A | 1/2014 |
| WO | WO 2012/147471 A1 | 11/2012 |
| WO | WO 2013/008702 A1 | 1/2013 |

OTHER PUBLICATIONS

International Search Report (PCT/ISA/210) issued in PCT Application No. PCT/JP2016/066753 dated Aug. 23, 2016 with English translation (Two (2) pages).
Japanese-language Written Opinion (PCT/ISA/237) issued in PCT Application No. PCT/JP2016/066753 dated Aug. 23, 2016 (Three (3) pages).

* cited by examiner

[FIG. 1]
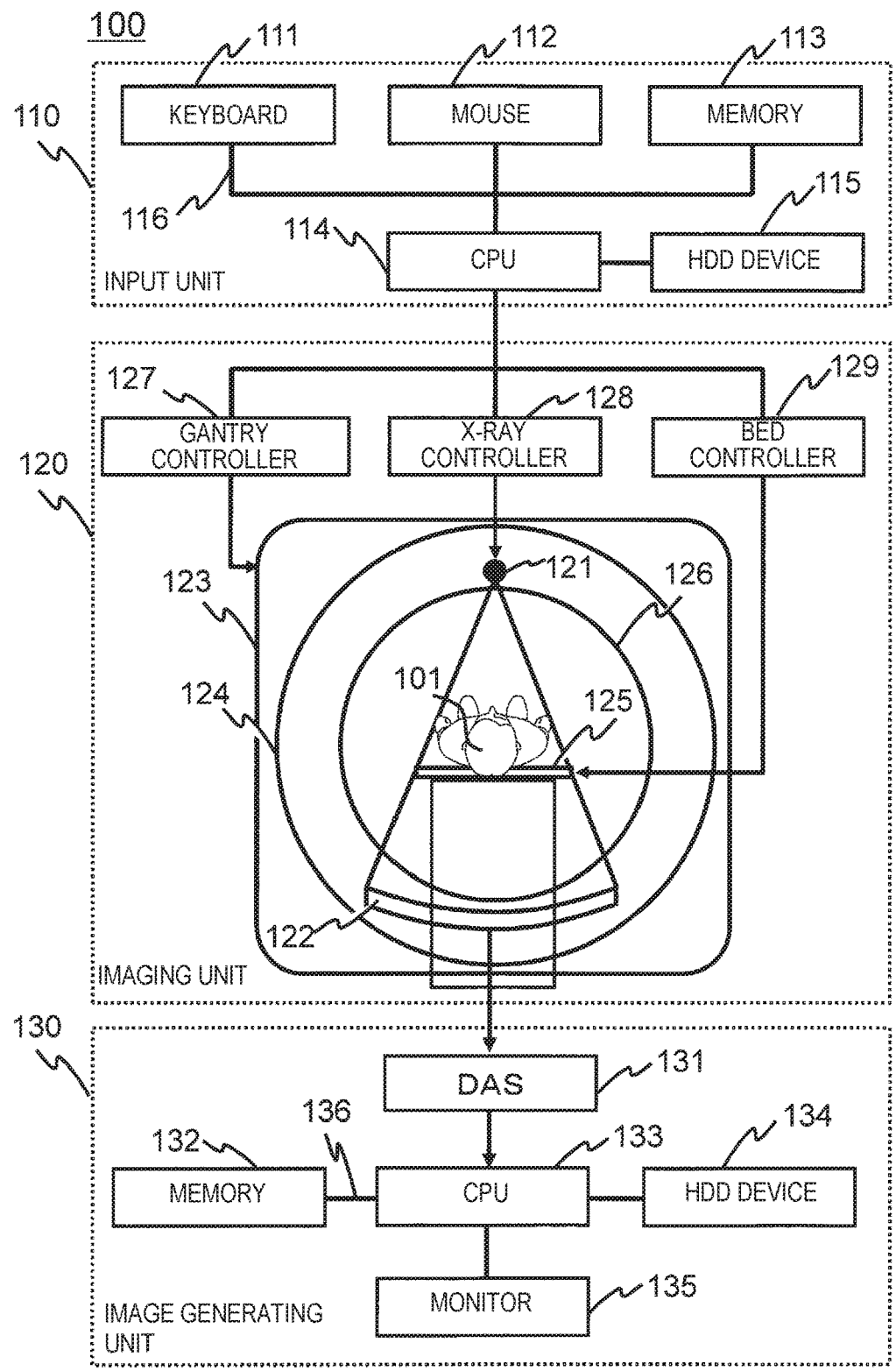

[FIG. 2]
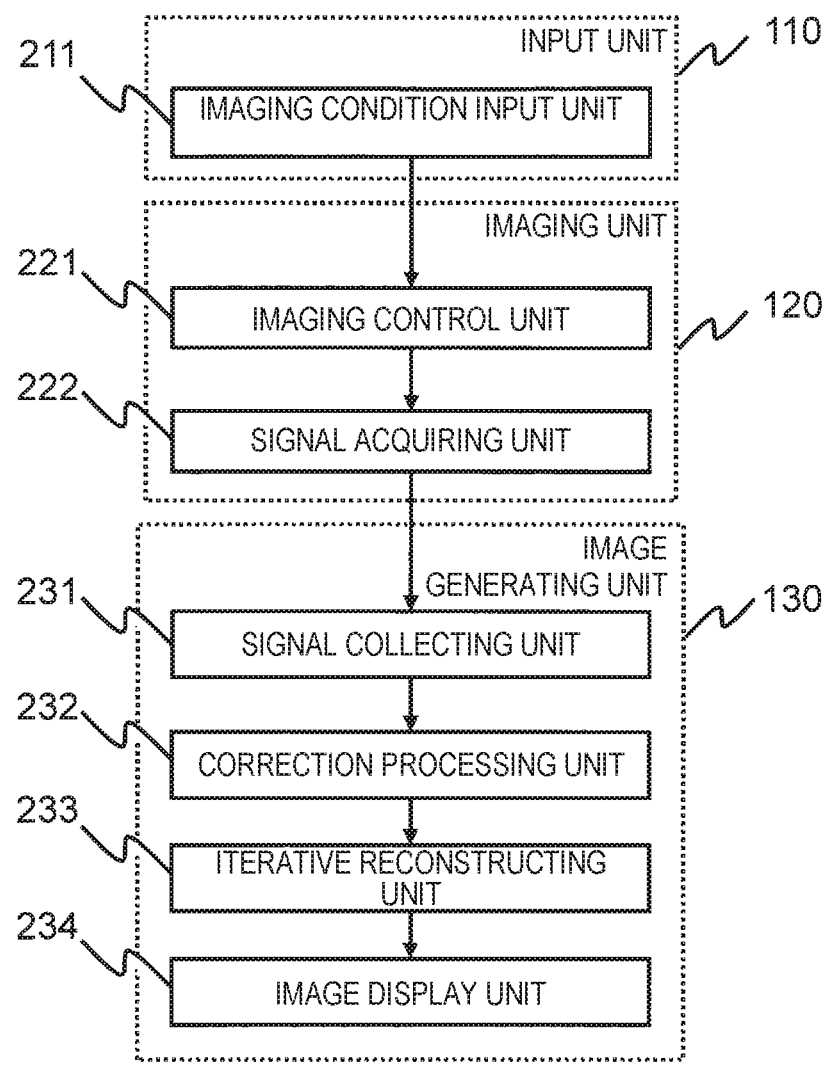

410 [X-RAY CONDITIONS]
TUBE VOLTAGE [120] kV    TUBE CURRENT TIME PRODUCT [200] mAs
NUMBER OF TIMES OF IMAGING [900] [TIMES/ROTATION]

420 [RECONFIGURATION RANGE]
FOV [700] mm
IMAGE CENTER  X: [0] mm  Y: [0] mm  Z: [0] mm

430 [WEIGHT CONDITIONS]
☑ CONSTANT VALUE   ☐ NUMBER OF PROTONS OF DETECTION ELEMENT

440 [IMAGING PORTION]
☑ HEAD  ☐ CHEST  ☐ ABDOMEN  ☐ LUNG FIELD  ...
☐ ELLIPTICAL APPROXIMATION  (LONG DIAMETER a [  ] mm,  SHORT DIAMETER b [  ] mm)

450 [DESIRED IMAGE QUALITY]
☑ FIXED NOISE REDUCTION RATE [75] %
☐ FIXED X-RAY DOSE REDUCTION RATE [  ] %
☐ FIXED NOISE VALUE [  ] HU

460 [RECONFIGURATION FILTER]
☑ HEAD  ☐ CHEST  ☐ ABDOMEN  ☐ LUNG FIELD  ...

470 [PROJECTION DATA CORRECTION]
☐ SMALL  ☐ MEDIUM  ☑ LARGE ...

480 [PROJECTION DATA RANGE]
(INITIAL IMAGE)     ☐ 180 DEGREES  ☑ 360 DEGREES  ☐ MAXIMUM COLLECTION VALUE  ...
(ITERATIVE CORRECTION)  ☐ 180 DEGREES  ☐ 360 DEGREES  ☑ MAXIMUM COLLECTION VALUE  ...

[FIG. 4]
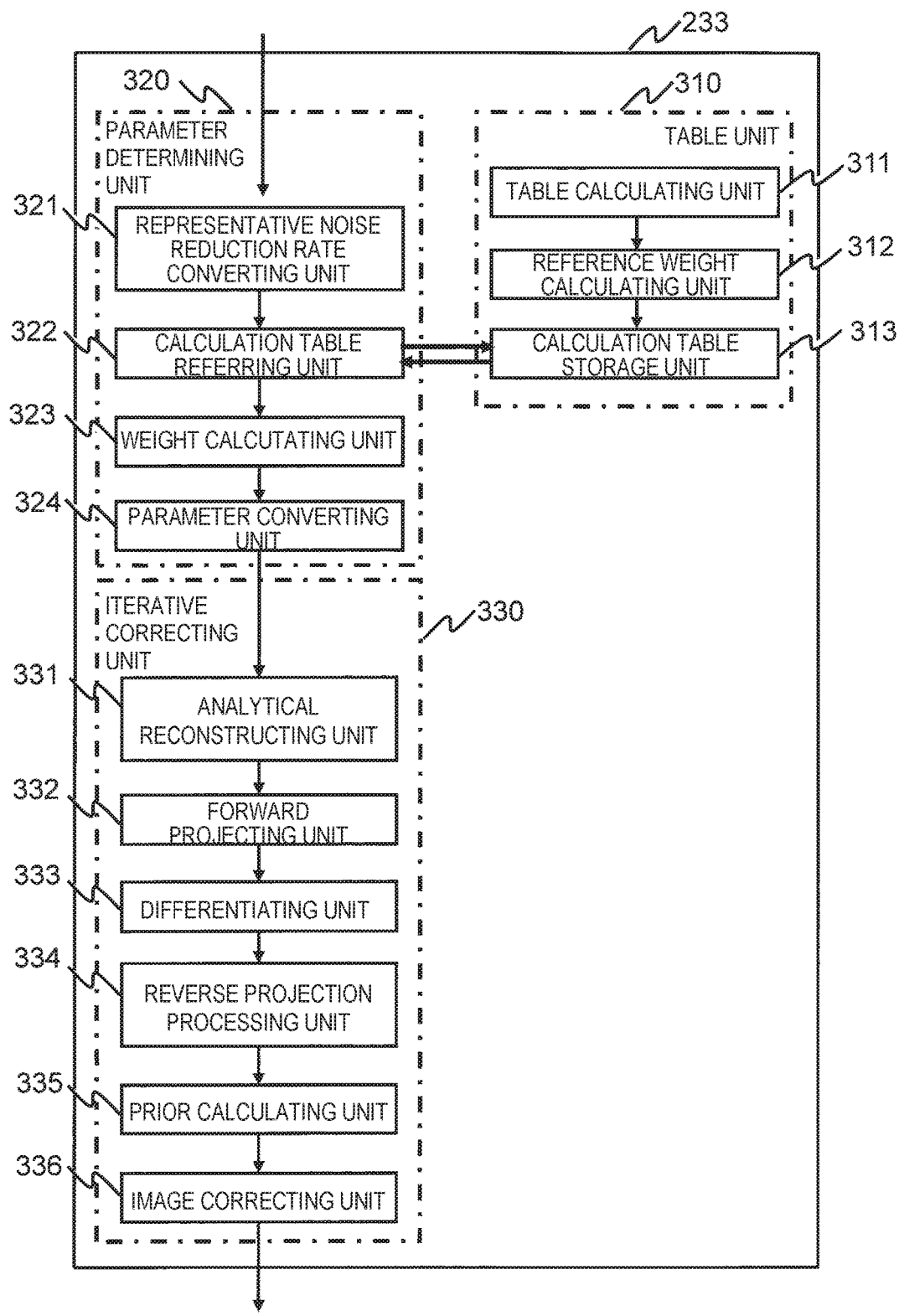

[FIG. 5]
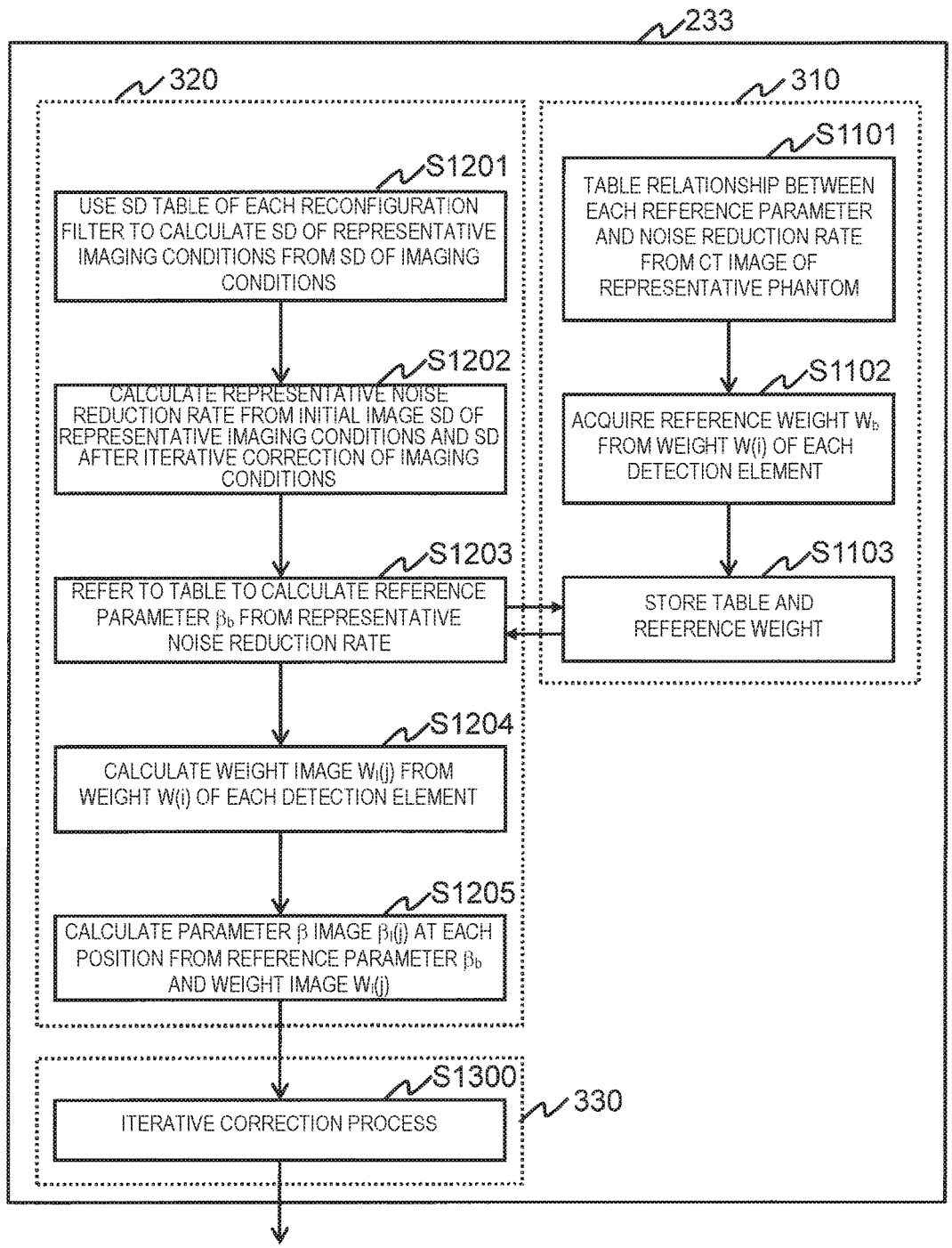

CT IMAGE OF EACH PARAMETER $\beta_b$ 510

NOISE REDUCTION RATE FOR EACH $\beta_b$

[FIG. 7]

| NUMBER OF TIMES OF ITERATION /711 | RECONFIGURATION FILTER /712 | ... | ※ APPROXIMATE CURVE (SECOND-ORDER EQUATION) /713 — 710 |
|---|---|---|---|
| 20 | Ramp | ... | $y = a_1 \cdot x^2 + b_1 \cdot x + c_1$ |
| 60 | Ramp | ... | $y = a_2 \cdot x^2 + b_2 \cdot x + c_2$ |
| ... | ... | ... | ... |

※ ASSUME NOISE REDUCTION RATE [%] AS X AND REFERENCE PARAMETER $\beta_b$ AS y

WEIGHT W(i) OF
DETECTION ELEMENT

WEIGHT IMAGE $W_i(j)$
AT EACH POSITION

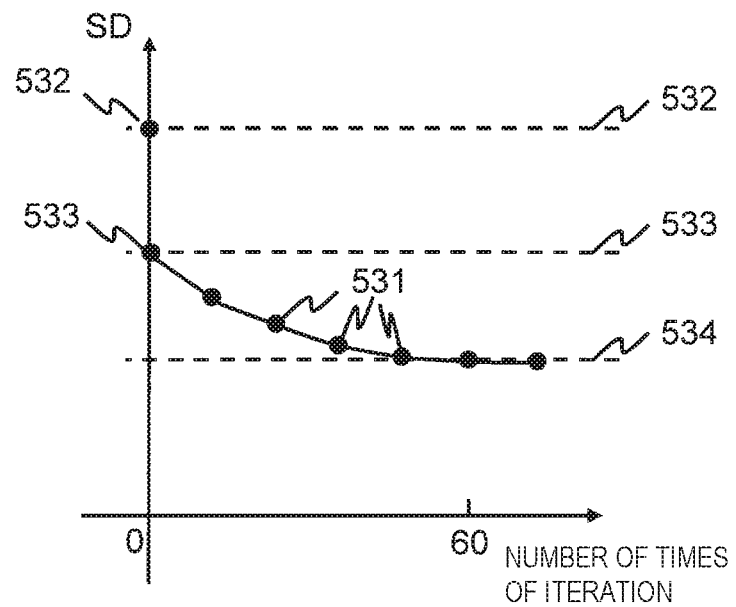

WEIGHT IMAGE $W_l(j)$ AT EACH POSITION

PARAMETER β IMAGE $β_l(j)$ AT EACH POSITION

[FIG. 11]
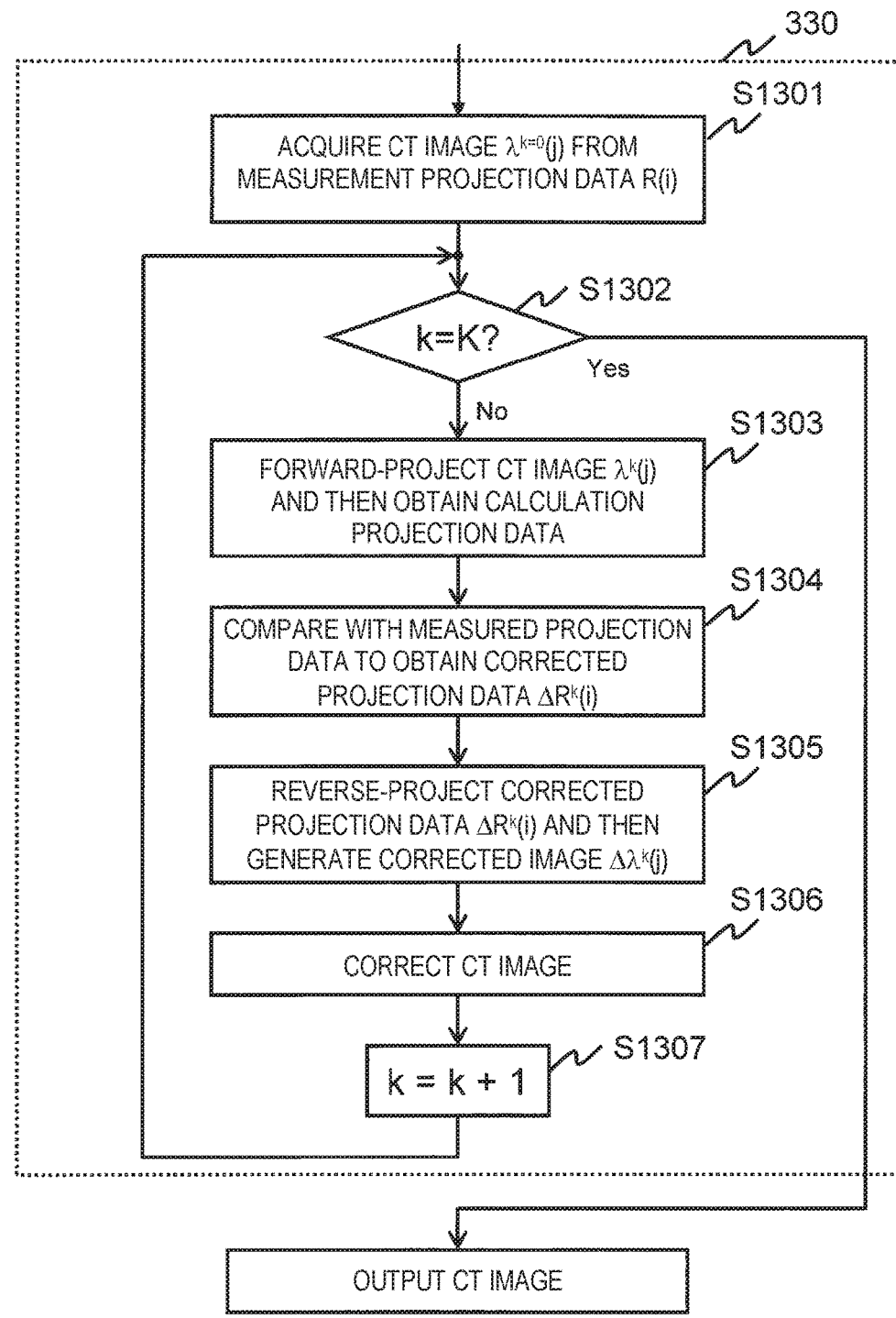

611

612

613

[FIG. 13]
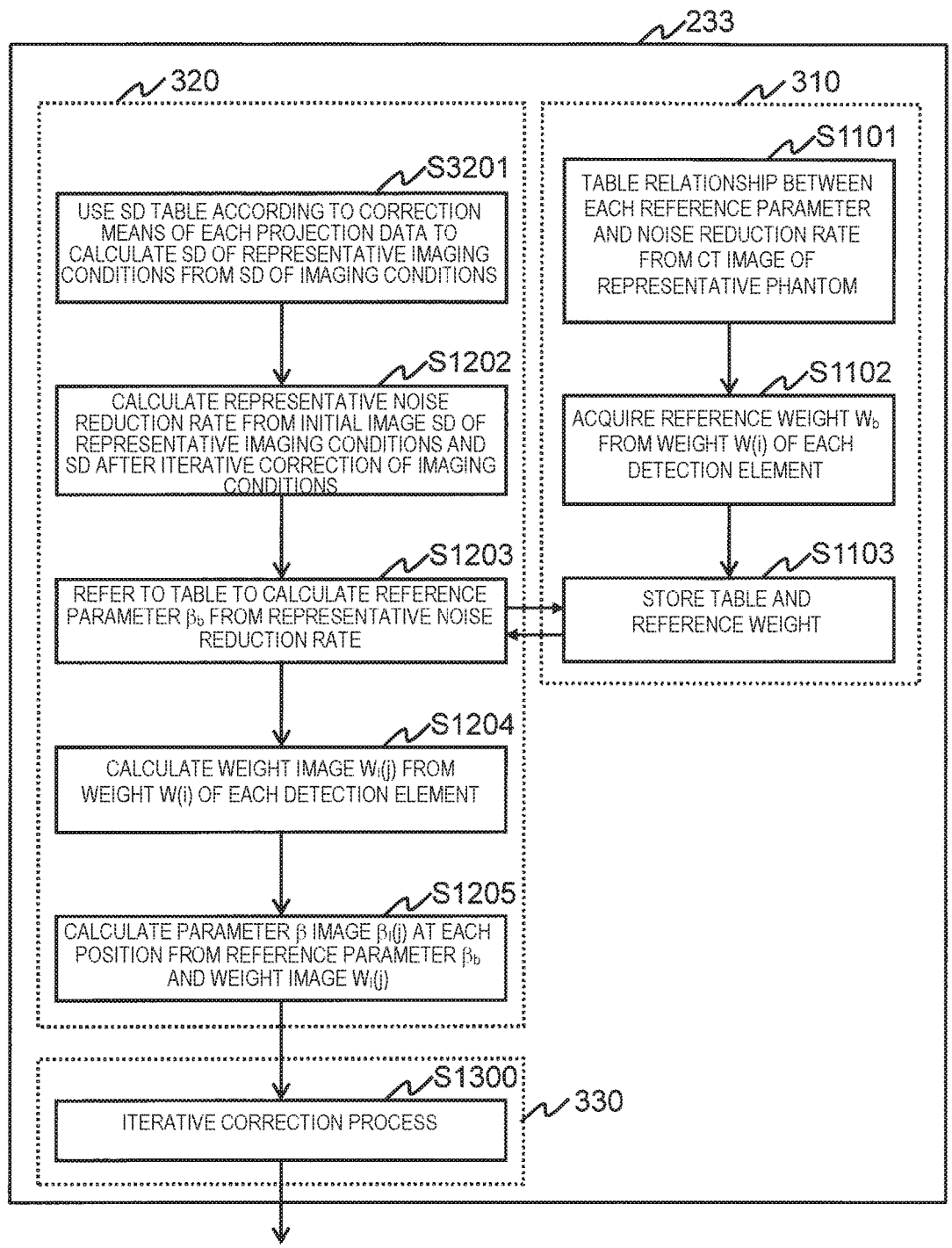

[FIG. 14]
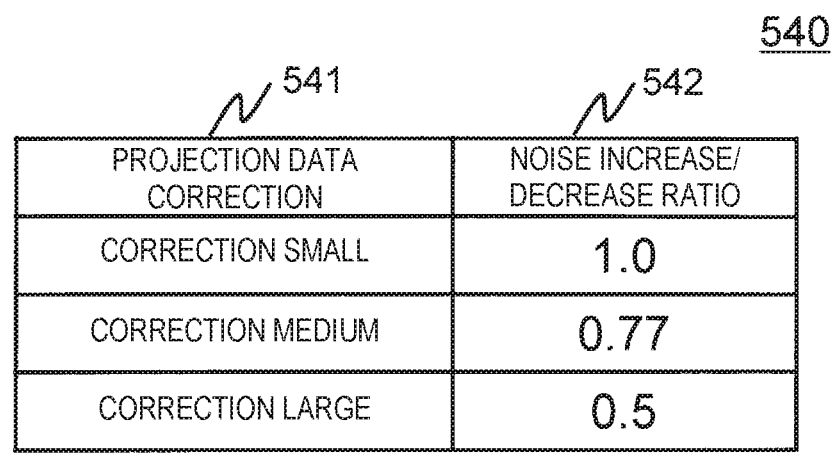

631
630
632 633

641
640
642 643

[FIG. 16]
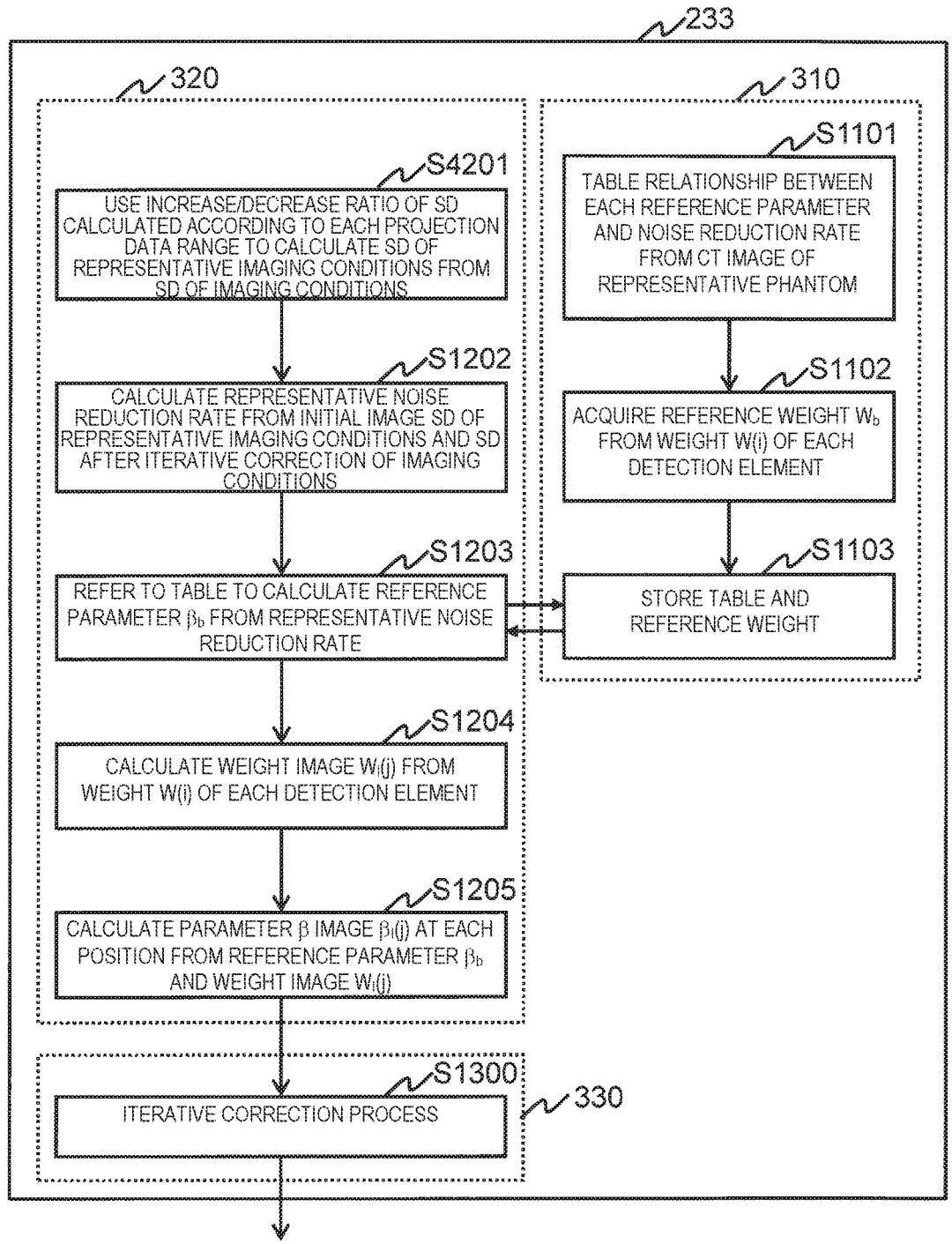

[FIG. 17]
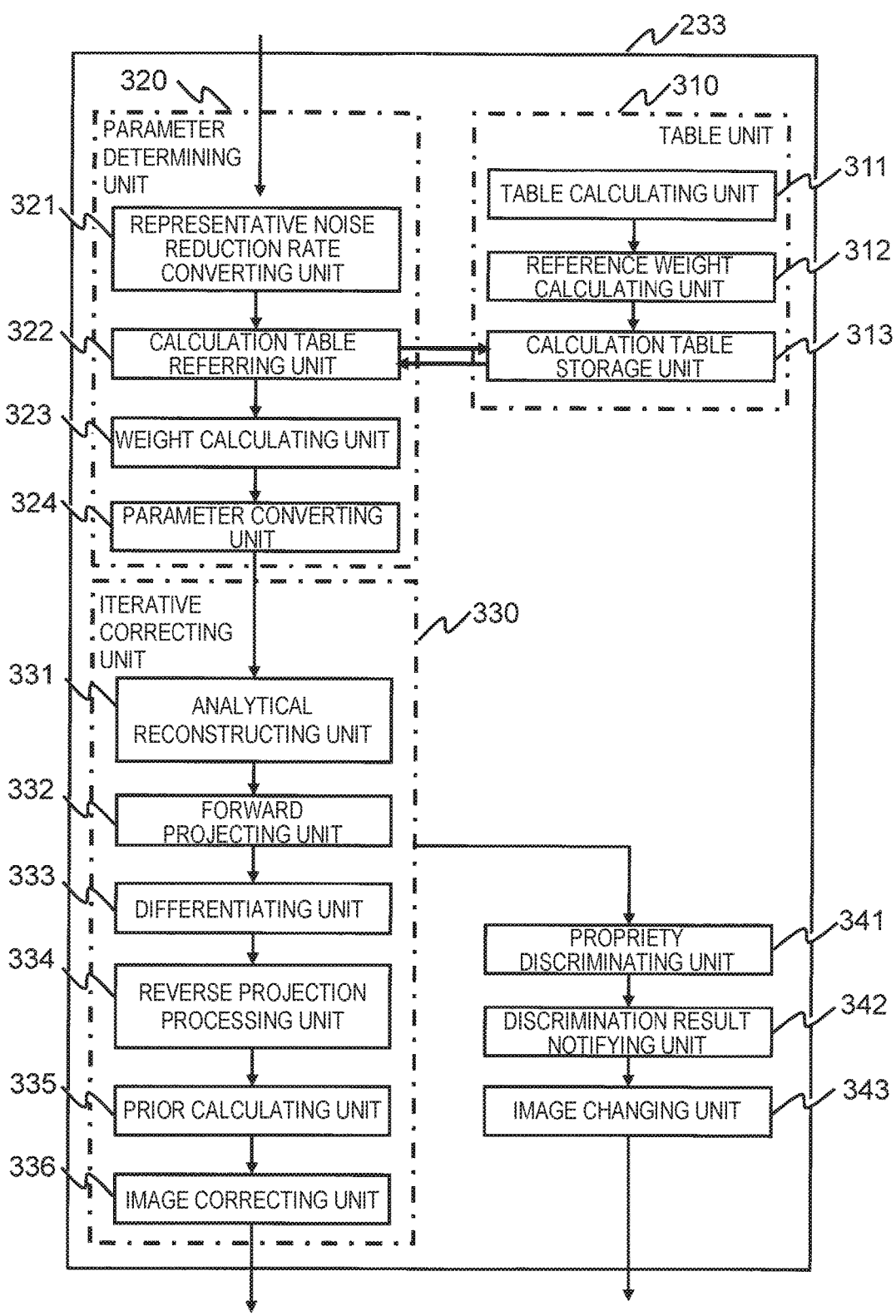

[FIG. 18]
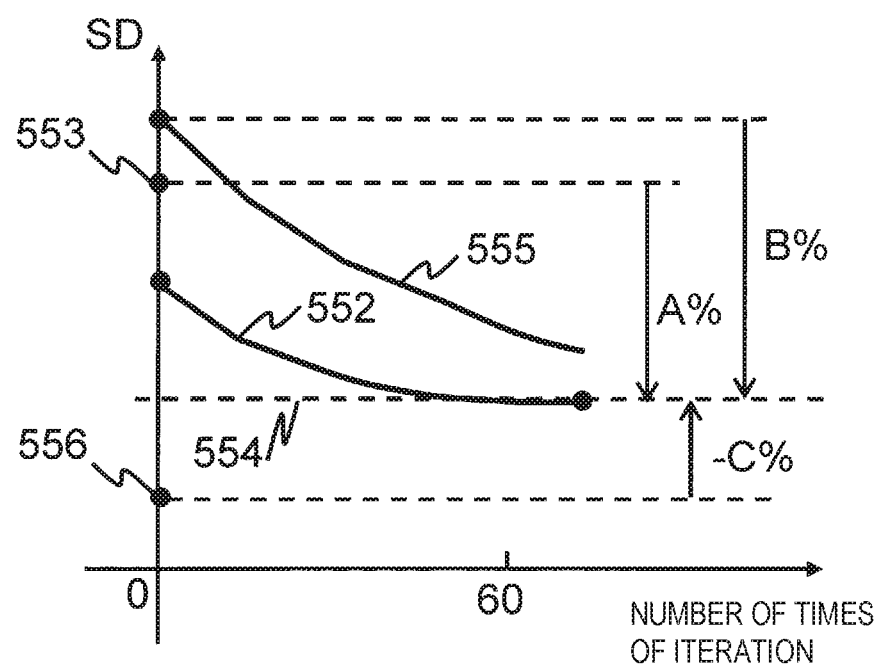

[FIG. 19]
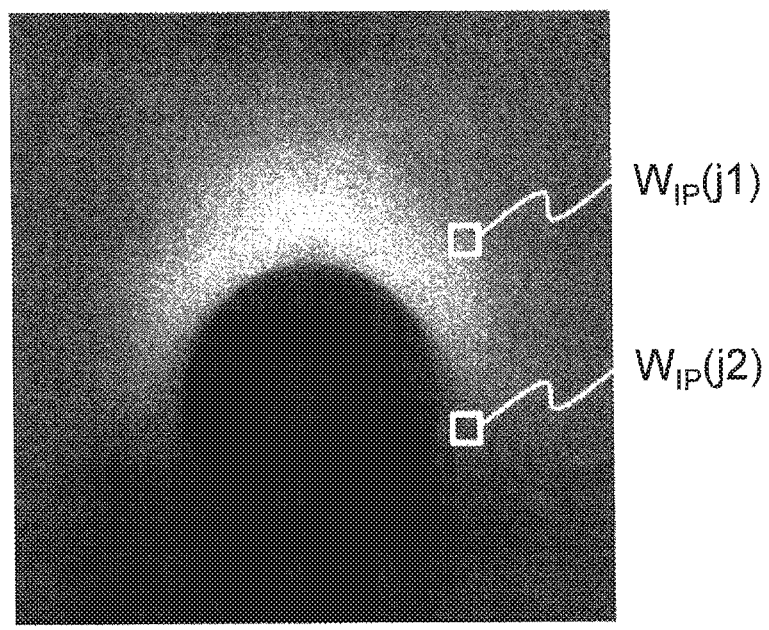

X-RAY CT DEVICE AND SEQUENTIAL CORRECTION PARAMETER DETERMINATION METHOD

TECHNICAL FIELD

The present invention relates to an X-ray CT (Computed Tomography) apparatus and particularly, to an iterative reconstruction technique for iteratively correcting a CT image.

BACKGROUND ART

An X-ray CT apparatus calculates an X-ray absorption coefficient (CT value) of each point in a subject from measured projection data obtained by imaging the subject from multiple directions to obtain a distribution image (CT image). As a technique for achieving both of low radiation exposure of a subject to X-ray and high image quality of the subject, there is a technique called an iterative reconstruction method (see, e.g., Patent Document 1). In the iterative reconstruction method, in order to make measured projection data obtained by an X-ray CT apparatus and calculated projection data calculated from a CT image generated from the measurement data equal to each other, the calculated projection data or the CT image is iteratively corrected, thereby reducing noises of the CT image at a low dose.

The iterative reconstruction method requires bigger calculation amount with iterative updating than an analytical method of calculating a CT value in the related art and also requires optimization of huge parameters. In particular, the iterative reconstruction method requires setting of many parameters to perform a smoothing process between adjacent pixels during updating to obtain a noise reduction effect.

As a method of reducing the calculation amount, there is a method of stopping iterative correction on a CT image output during the iterative correction or changing parameters at the point of time when a noise of the CT image, here, a measurement value of the standard deviation (hereinafter referred to as "SD") representing the variation of a CT value, reaches a desired value (see, e.g., Patent Document 2).

PRIOR ART DOCUMENT

Patent Document

Patent Document 1: JP-A-2006-25868
Patent Document 2: JP Patent No. 4535795

SUMMARY OF THE INVENTION

Technical Problem

According to the technique disclosed in Patent Document 2, it is necessary to measure the SD in the CT image being corrected iteratively. Since the SD has to be measured under the condition where a region of interest (hereinafter referred to as "ROI") is set for a tissue composed of uniform CT values, it is difficult to accurately measure the SD when an imaging object is a tissue composed of different CT values.

In order to obtain a desired SD, a method may be considered in which optimized reconstruction parameters are retained in a table for the imaging conditions such as an X-ray tube and abed speed presumed before imaging. However, since the number of imaging conditions is enormous, a lot of man-hours are required to create the table. In addition, the number of tables retaining parameters also increases.

The present invention has been made in view of the above circumstances and an object of the present invention is to achieve both high quality image and low radiation exposure without increasing man-hours and the amount of data to be retained.

Solution to Problem

According to an aspect of the present invention, a table of iterative correction parameters optimized in the representative imaging conditions is held and an iterative correction parameter optimized in the actual imaging conditions is determined from the iterative correction parameters held in the table. In addition to the parameter table, a reference weight is also held and is reflected to generate the iterative correction parameter for each pixel position.

Advantageous Effects of the Invention

According to the present invention, both high quality image and low radiation exposure may be achieved without increasing man-hours and the amount of data to be retained.

BRIEF DESCRIPTION OF THE DRAWINGS

FIG. 1 is a block diagram of a hardware configuration of each unit of an X-ray CT apparatus according to a first embodiment.

FIG. 2 is a functional block diagram of an X-ray CT apparatus according to the first embodiment.

FIG. 3 is an explanatory view for explaining an example of a imaging condition reception screen according to the first embodiment.

FIG. 4 is a functional block diagram of an iterative reconstruction unit according to the first embodiment.

FIG. 5 is a flowchart of a process by a parameter determining unit and a table unit in an iterative correction process according to the first embodiment.

FIG. 7 is an explanatory view for explaining an example of a parameter table of the first embodiment.

FIG. 9A is an explanatory view for explaining the relationship between the number of times of iteration and a noise in an iterative correction process of the first embodiment. FIG. 9B is an explanatory view for explaining an example of a noise table of the first embodiment.

FIG. 11 is a flowchart of an iterative correction process by an iterative correcting unit of the first embodiment.

FIG. 13 is a flowchart of a process by a parameter determining unit and a table unit in an iterative correction process of a second embodiment.

FIG. 14 is an explanatory view for explaining an example of a noise table in a correction method of the second embodiment.

FIG. 16 is a flowchart of a process by a parameter determining unit and a table unit in an iterative correction process of a third embodiment.

FIG. 17 is a functional block diagram of an iterative reconstructing unit of a fourth embodiment.

FIG. 18 is an explanatory view for explaining a process by a representative noise reduction rate converting unit of the fourth embodiment.

FIG. 19 is an explanatory view for explaining a weight image according to a modification of the embodiment of the present invention.

DESCRIPTION OF EMBODIMENTS

First Embodiment

Figure 6A:
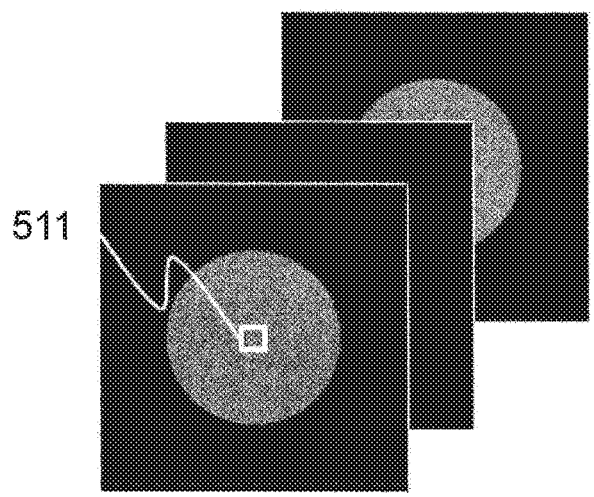
FIG. 6A is an explanatory view for explaining a process by a table calculating unit of the first embodiment.

A first embodiment of the present invention will be described with reference to the drawings. Hereinafter, throughout the drawings for explaining embodiments of the present invention, the elements having basically the same functions are denoted by the same reference numerals and explanation thereof will not be repeated.

[X-Ray CT Apparatus]

First, an X-ray CT apparatus according to the present embodiment will be described. The X-ray CT apparatus is an apparatus for obtaining an X-ray absorption coefficient distribution image by calculating an X-ray absorption coefficient of each point in a subject from measured projection data obtained by imaging the subject from multiple directions. The X-ray absorption coefficient of each point is normalized with air as −1000 and water as 0. Hereinafter, the normalized X-ray absorption coefficient is called a CT value and the X-ray absorption coefficient distribution image is called a CT image.

FIG. 1 illustrates a hardware configuration of an X-ray CT apparatus 100 according to the present embodiment. In addition, FIG. 2 illustrates a block diagram of functions implemented by software of the X-ray CT apparatus 100 of the present embodiment.

As illustrated in these figures, the X-ray CT apparatus 100 of the present embodiment includes an input unit 110, a imaging unit 120, and an image generating unit 130.

[Input Unit]

The input unit 110 functions as a imaging condition input unit 211 for inputting imaging conditions. The imaging condition input unit 211 of the present embodiment displays a imaging condition reception screen on a monitor, receives the input of the imaging conditions through the screen, and sets the received imaging conditions. The details of the imaging condition reception screen and the imaging conditions received through the screen will be described later.

As illustrated in FIG. 1, the input unit 110 has a hardware configuration of a general-purpose computer and includes a keyboard 111 and a mouse 112 which are input/output interfaces, a memory 113 and a hard disk drive (HDD) 115 which store data, a central processing unit (CPU) 114 which performs an arithmetic process, and the like. Further, the input unit 110 includes a monitor (not illustrated). The various elements in the input unit 110 are interconnected by a data bus 116.

The keyboard 111 and the mouse 112 are used to input the imaging conditions and the like. Other input means such as a pen tablet or a touch panel may be provided for the input of the imaging conditions. Data input by the keyboard 111 or the like is transferred to the CPU 114 which is a processing unit.

The CPU 114 functions as the imaging condition input unit 211 by expansion/activation a predetermined program stored in advance in the memory 113, the HDD device 115, or the like. In addition, the CPU 114 functions as a portion of a imaging control unit 221 of the imaging unit 120 by sending a control signal to the imaging unit 120 by expansion/activation another program.

All or some of functions implemented by the CPU 114 may be implemented by hardware such as an application specific integrated circuit (ASIC) and a field programmable gate array (FPGA). Various data used to process each function and various data generated during processing are stored in the memory 113, the HDD device 115, and the like.

[Imaging Unit]

As illustrated in FIG. 2, the imaging unit 120 functions as the imaging control unit 221 that controls each unit to execute imaging, based on the imaging conditions input through the imaging condition input unit 211, and a signal acquiring unit 222 that irradiates and detects an X-ray. With these functions, the imaging unit 120 performs X-ray imaging according to the received imaging conditions to obtain measured projection data.

As illustrated in FIG. 1, the signal acquiring unit 222 includes an X-ray generating unit 121 that generates an X-ray according to the set imaging conditions, an X-ray detecting unit 122 that detects the X-ray passed through a subject 101 to obtain measured projection data, and a mechanism on which the X-ray generating unit 121 and the X-ray detecting unit 122 are mounted and that is rotated around the subject 101. This mechanism includes a gantry 123, a rotating plate 124 mounted with the X-ray generating unit 121 and the X-ray detecting unit 122 thereon so as to be rotated around the subject 101, and a circular opening 126 into which abed 125 on which the subject 101 is placed is inserted.

As in the general X-ray CT apparatus, the X-ray generating unit 121 irradiates the subject 101 with the X-ray and the X-ray detecting unit 122 detects the X-ray transmitted through the subject 101. The X-ray detecting unit 122 includes known X-ray detection elements (hereinafter, simply referred to as detection elements), each of which is composed of a scintillator, a photodiode, and the like, which are arranged in a channel direction, that is, a direction along an arc equidistant from the X-ray generating unit 121 in a plane parallel to the main plane of the rotating plate 124, and in a slice direction, that is, a body axial direction of the subject 101.

A typical example of the distance between an X-ray generation point of the X-ray generating unit 121 and an X-ray input surface of the X-ray detecting unit 122 is 1000 [mm]. A typical example of the diameter of the opening 126 is 700 [mm]. A typical example of time required for one rotation of the rotating plate 124 is 1.0 [s].

For example, the number of detection elements in the channel direction (hereinafter, referred to as a channel number) is 1,000. A typical example of size of each detection element in the channel direction is 1 [mm]. The number of times of imaging during one revolution of the rotating plate 124 is 900 and one imaging is performed every time the rotating plate 124 is rotated by 0.4 degrees. An angle of the rotating plate 124 at the time of imaging is called a projection angle. These specifications are not limited to the above values, but various modifications may be made depending on the configuration of the X-ray CT apparatus 100.

As illustrated in FIG. 1, the imaging control unit 221 includes a gantry controller 127 which controls the rotational operation of the rotating plate 124, an X-ray controller 128 which controls the operations of the X-ray generating unit 121 and the X-ray detecting unit 122, and a bed controller 129 which controls the position of the bed 125. The gantry controller 127, the X-ray controller 128, and the bed controller 129 control their respective units according to an instruction from the CPU 114.

Upon receiving from a user an instruction to start imaging, the CPU 114 instructs the gantry controller 127 to start rotating the rotating plate 124. The rotating plate 124 is driven by a driving motor. At the time when the rotation of the rotating plate 124 enters a constant speed state and the arrangement of the subject 101 at a imaging position is completed, the CPU 114 issues an instruction of an X-ray irradiation timing to the X-ray controller 128 and issues an instruction of an X-ray detection timing to the X-ray detecting unit 122.

Next, the imaging unit 120 in FIG. 2 performs X-ray imaging in accordance with the imaging conditions received by the imaging condition input unit 211. When the user uses the mouse 112, the keyboard 111, or the like to issue an instruction to start the imaging, the CPU 114 outputs a control signal to the bed controller 129 and the gantry controller 127 of the imaging control unit 221. In response to the control signal, the bed controller 129 moves the bed 125 along the rotation axis of the rotating plate 124 and stops the bed 125 at the time when a portion of the subject 101 to be imaged coincides with a passage range of X-ray between the X-ray generating unit 121 and the X-ray detecting unit 122, that is, a imaging position. Thus, the arrangement of the subject 101 at the imaging position is completed.

In addition, the gantry controller 127 starts the rotation of the rotating plate 124 by means of the driving motor at the same time when the start of imaging is instructed by the CPU 114. When the rotation of the rotating plate 124 enters the constant speed state and the arrangement of the subject 101 at the imaging position is completed, the CPU 114 issues an instruction of an X-ray irradiation timing to the X-ray controller 128 and issues an instruction of an X-ray imaging timing to the X-ray detecting unit 122. According to this instruction, the X-ray controller 128 causes the X-ray generating unit 121 to irradiate the subject 101 with the X-ray and causes the X-ray detecting unit 122 to detect the X-ray to start the imaging. Further, the X-ray controller 128 determines an energy spectrum and an output amount of the X-ray with which the subject 101 is irradiated, for example, by a tube voltage and a tube current time product of the X-ray generator 121, which are set by the user.

Although an example of using the X-ray having one type of energy spectrum has been described here, the configuration of this embodiment may also be applied to a multi-energy CT. In that case, control is performed so as to acquire imaging data, for example, by switching a tube voltage at a high speed everyone revolution or during one revolution to irradiate the subject 101 with an X-ray having two or more types of energy spectra.

In addition, in the X-ray CT apparatus 100 of the present embodiment, a subject means an object to be imaged and includes the subject 101 and the bed 125 supporting the subject 101. The subject 101 is not limited to a human body but may be an object to be inspected such as a phantom or a machine.

[Image Generating Unit]

The image generating unit 130 reconstructs a CT image from a signal detected (measured projection data acquired) by the imaging unit 120. The CT image is expressed by superimposing tomographic planes of the subject in the body axial direction. The CT image is clinically useful at medical sites because it may be used to diagnose the patient's medical conditions accurately and immediately. However, the subject undergoes a certain amount of radiation exposure under the conditions of obtaining high image quality necessary for doctor's diagnosis.

If the X-ray dose is lowered to achieve low radiation exposure, the ratio of a noise to a detected signal increases, which results in a large amount of linear streak artifacts and granular noises which cause misdiagnosis. Therefore, it is required to achieve both high image quality and low radiation exposure by reducing streak artifacts and noises during low dose imaging.

To meet this requirement, the image generating unit 130 of the present embodiment generates a final output image by an iterative reconstruction method.

To this end, as illustrated in FIG. 1, the image generating unit 130 of the present embodiment includes a data acquisition system (hereinafter referred to as "DAS") 131, a memory 132 that stores data, an HDD device 134, a central processing unit (CPU) 133 that performs an arithmetic process, and a display unit (monitor) 135 that displays results of the process, and the like, all of which are interconnected by a data bus 136.

First, the image generating unit 130 generates a CT image (initial image) from the measured projection data. Then, the initial image is iteratively reconstructed (iteratively corrected) so that calculated projection data calculated by forward projection calculation from the initial image becomes equal to the measured projection data.

To this end, the image generating unit 130 of the present embodiment includes a signal collecting unit 231 that performs an AD conversion for converting a signal detected by the X-ray detecting unit 122 of the signal acquiring unit 222 into a digital signal, a correction processing unit 232 that corrects the measured projection data converted into the digital signal, an iterative reconstructing unit 233 that reconstructs the CT image from the corrected measured projection data, and an image display unit 234 that outputs the reconstructed CT image.

The signal collecting unit 231 of the image generating unit 130 converts the output signal of the X-ray detecting unit 122 into a digital signal which is then stored in the memory 132. The signal collecting unit 231 is implemented by the DAS 131. That is, the signal detected by the X-ray detecting unit 122 of the imaging unit 120 is collected by the DAS 131 functioning as the signal collecting unit 231 and is converted into a digital signal which is then delivered to the CPU 133.

The correction processing unit 232 performs correction on the measured projection data processed by the signal collecting unit 231, such as offset correction for calibrating a zero value of the X-ray detection signal, reference correction for correcting the variation of a signal component detected for each projection angle, a known air calibration process for correcting the sensitivity between detection elements, and so on. The corrected measured projection data is sent to the iterative reconstructing unit 233.

In this manner, the measured projection data obtained by the X-ray detecting unit 122 is subjected to the correction process in the correction processing unit 232 before the iterative correction. Hereinafter, the corrected measured projection data is referred to as measured projection data.

The iterative reconstructing unit 233 generates a CT image from the measured projection data. At this time, the CT image is iteratively corrected so as to reduce a difference between the measured projection data and the calculated projection data obtained by the forward projection calculation from the CT image generated from the measured projection data. In the present embodiment, the iterative correction of the CT image is performed so as to implement a desired noise reduction rate or X-ray dose reduction rate. The noise reduction rate or the X-ray dose reduction rate is controlled by selection of a parameter used at the time of iterative correction (iterative correction parameter).

For the iterative correction, the iterative reconstructing unit 233 performs a calculation using a difference between the measured projection data and the calculated projection data to correct the CT image so as to reduce this difference (first calculation), and a calculation using a CT value difference between two or more pixels of the CT image before correction to correct the CT image so as to reduce this CT value difference (second calculation), in an iterative manner.

As the first calculation, for example, a Likelihood calculation or a Datafit calculation is performed, both of which will be hereinafter represented as the Likelihood calculation. As the second calculation, a Prior calculation or a Regularization calculation is performed, both of which will be hereinafter represented as the Prior calculation. The iterative correction parameter is used as a coefficient of this Prior calculation. In addition, the iterative correction parameter may be used as a coefficient of the Likelihood calculation instead of the coefficient of the Prior calculation.

The iterative reconstructing unit 233 of the present embodiment calculates in advance and holds the relationship between a targeted noise reduction rate or X-ray dose reduction rate and the iterative correction parameter in the representative imaging conditions. Then, at the time of actual imaging, a noise reduction rate or X-ray dose reduction rate designated (desired) in the actual imaging conditions is converted into the noise reduction rate or X-ray dose reduction rate in the representative imaging conditions and an iterative correction parameter corresponding to the converted reduction rate is determined and used for the iterative correction. The iterative correcting process by the iterative reconstructing unit 233 of the present embodiment will be described in detail later.

The image display unit 234 displays the CT image iteratively corrected by the iterative reconstructing unit 233. The image display unit 234 is implemented by the monitor 135.

The correction processing unit 232 and the iterative reconstructing unit 233 are implemented by the CPU 133 expanding and executing a predetermined program stored in advance in the memory 132, the HDD device 134, and the like.

That is, the CPU 133 functions as the correction processing unit 232 to perform correction on a signal and also functions as the iterative reconstructing unit 233 to use the iterative processing to reconstruct an image. In addition, data is stored in the HDD device 134 and the like and is input and output to the outside as necessary. The CT image obtained by the image reconstruction is displayed on the monitor 135 such as a liquid crystal display or a CRT that functions as the image display unit 234.

All or some of the functions implemented by the CPU 133 may be implemented with hardware such as the ASIC (Application Specific Integrated Circuit) and the FPGA (Field Programmable Gate Array). Various data used for processing of each function and various data generated during processing are stored in the memory 132, the HDD device 134, and the like.

Further, the signal collecting unit 231 may be included in the signal acquiring unit 222. In this case, the imaging unit 120 outputs a digital signal. For example, when the image generating unit 130 is connected via a network, this configuration is preferable.

Further, the input unit 110 and the image generating unit 130 may be independent hardware or may be configured to share the hardware. Therefore, as described above, the CPU 133, the memory 132, the monitor 135, and the like may be used in common with the input unit 110.

[Imaging Condition Reception Screen]

Here, a imaging condition reception screen which is displayed on the monitor by the imaging condition input unit 211 and receives input of the imaging conditions will be described. FIG. 3 illustrates an example of the imaging condition reception screen 400 of the present embodiment.

The imaging condition reception screen 400 of the present embodiment includes an X-ray condition setting area 410 for setting a tube voltage and a tube current time product corresponding to the energy and output amount of X-ray with which the subject 101 is to be irradiated, and the number of times of imaging per rotation, a reconstruction range setting area 420 for setting a range of reconstructed image, a weight setting area 430 for selecting a weight used for iterative reconstruction, a imaging portion setting area 440 for setting a imaging portion, a imaging/image setting area 450 for selecting a desired image quality, a reconstruction filter setting area 460 for selecting a reconstruction filter, a projection data correction setting area 470 for selecting a measured projection data correction method, and a projection data range setting area 480 for selecting a CT image reconstructed from projection data (hereinafter, referred to as an initial image) or a range of measured projection data to be used for iterative correction.

While watching the imaging condition reception screen 400 displayed on the monitor, the user operates the mouse 112, the keyboard 111, etc. to set the X-ray conditions in the X-ray condition setting area 410, the reconstruction range in the reconstruction range setting area 420, the weight conditions in the weight setting area 430, the imaging portion in the imaging portion setting area 440, the desired image quality in the imaging/image setting area 450, the reconstruction filter conditions in the reconstruction filter setting area 460, the measured projection data correction method in the projection data correction setting area 470, and the initial image or the range of measured projection data to be used for iterative correction in the projection data range setting area 480, which will be described in more detail below.

FIG. 3 illustrates one example in which a tube voltage value of 120 [kV], a tube current time product of 200 [mAs], and the number of times of imaging of 900 [times/rotation] are set in the X-ray condition setting area 410 by the user. An example of using the X-ray having one type of energy spectrum is illustrated in FIG. 3. However, in the case of multi-energy CT using two or more types of X-rays, the items of tube voltage, tube current time product, and the number of times of imaging are added to the X-ray condition setting area 410 and are set for each type of X-rays in the same manner.

The user sets a reconstruction range (or a Field Of View (FOV)), which is an area for image reconstruction, in the reconfiguration range setting area 420. The FOV is set by setting the size and center position of the FOV. In the present embodiment, as an example, the FOV is defined as a square. In the example of FIG. 3, for the FOV, one side is set to 700 mm and the center position is set to X=Y=Z=0 [mm], which is equal to the rotation center of the X-ray CT apparatus 100. However, the FOV is not limited to the square but may be set to any shape such as a circle, a rectangle, a cube, a rectangular parallelepiped, a sphere, or the like, in which case the configuration of this embodiment may be applied as well.

The weight setting area 430 sets the type of weight to be given to a difference between the measured projection data detected by each detection element of the X-ray detecting unit 122 and the calculated projection data calculated by the forward projection calculation. The type of weight is selected from two types of "constant value" for keeping the weights given to data of all the detection elements constant and "the number of photons of detection element" for giving a weight according to the number of X-ray photons detected by the detection element. As used herein, the number of X-ray photons refers to an estimation of the number of X-ray photons detected by a known photon counting type of detection element or the number of X-ray photons detected by a detection element using the inverse logarithmic conversion from the measured projection data after being converted into the above-mentioned digital signal. Here, a case where "constant value" is selected will be exemplified. Hereinafter, in the present specification, the weight given to the difference between the measured projection data detected by each detection element and the calculated projection data calculated by the forward projection calculation is simply referred to as a detection element weight.

The imaging portion setting area 440 receives a selection of the imaging portion. In the present embodiment, the imaging portion setting area 440 receives a selection from enumerated X-ray irradiation targets (parts and tissues such as the head, chest, lung field, and the like) or a designation of a numerical value with the condition that the X-ray irradiation targets have an approximate ellipsoid. Here, a case where "head" is selected from the enumerated X-ray irradiation targets will be exemplified.

The imaging/image setting area 450 receives a selection of desired image quality. In the present embodiment, for example, a selection is received from enumerated modes and a reduction rate or a noise value is received as a numerical value.

Here, the modes include a mode for acquiring a CT image that achieves a desired noise reduction rate ("fixed noise reduction rate"), a mode for acquiring a CT image that achieves a desired X-ray dose reduction rate ("fixed X-ray dose reduction rate"), and a mode for acquiring a CT image that achieves a desired noise value ("fixed noise value"). The user selects one of these modes and designates a target value.

FIG. 3 exemplifies a case where the mode for acquiring a CT image that achieves a desired noise reduction rate is selected and the target value of the reduction rate is 75%. This indicates that a CT image in which the noise of the initial image is reduced by 75% is obtained by using the iterative correction to be described later.

The "fixed X-ray dose reduction rate" is a mode for acquiring the same image noise as a CT image obtained by analytically reconstructing data imaged with the X-ray dose before reduction when imaging with the X-ray dose corresponding to the designated X-ray dose reduction rate. The "fixed noise value" is a mode for acquiring a CT image having a desired noise value using the iterative correction.

In the present embodiment, as will be described later, the noise reduction rate is calculated based on the initial image input for the iterative correction. However, in addition to the initial image, the noise reduction rate may be calculated based on a CT image output from the X-ray CT apparatus 100 before the iterative correction (hereinafter, referred to as an apparatus output image). Hereinafter, since the initial image and the apparatus output image may be handled in the same manner, description of the apparatus output image will be omitted, and the initial image will be explained.

The reconstruction filter setting area 460 is an area for receiving the type of reconstruction filter to be applied to the initial image used for the iterative correction. The reconstruction filter determines the image quality of the initial image serving as a reference for determining the noise reduction amount. Here, since this reconstruction filter is often determined depending on parts, the reconstruction filter setting area 460 receives the type of reconstruction filter by receiving a designation of a part. Generally, the reconstruction filter used at the time of imaging the head, the lung field, etc. has an effect of acquiring a high-resolution and high-noise CT image. In the meantime, the reconstruction filter used at the time of imaging the abdomen has an effect of acquiring a low-resolution and low-noise CT image. A case where a filter for the head is designated is exemplified in FIG. 3.

The projection data correction setting area 470 is an area for receiving a designation of the measured projection data correction method used for the initial image. As the correction effect increases, data of a detection element in the channel direction, the projection angle direction, or the column direction may be smoothed with data of an adjacent detection element to reduce the noise of the data of the detection element. Here, the correction effect is divided in steps by its size and a designation is received at the step of size. A case where the correction method is classified as small, medium, and large according to the size of the correction effect and large is selected is exemplified in FIG. 3.

The projection data range setting area 480 is an area for receiving a designation of a range of measured projection data to be used for generation (reconstruction) of the initial image and the iterative correction to be described later. Here, the projection data range setting area 480 receives a designation of a projection angle or the like. For example, when the measured projection data range corresponding to the projection angle of 180 degrees is used, high temporal resolution may be obtained. Further, when the measured projection data range corresponding to the projection angle of 360 degrees is used, noise may be suppressed. Further, in a known helical scan, the range of measured projection data collected at each pixel position of the CT image is changed depending on a beam pitch obtained by dividing a bed moving distance [mm] by a beam width [mm] of the X-ray. In addition, it is also possible to make a designation using all data collected at each pixel position of the CT image (a maximum collection value). A case where the measured projection data range of 360 degrees is used for the initial image and a selection is made so as to use all data for the iterative correction.

The imaging condition reception screen 400 is not limited to the screen configuration of FIG. 3. In addition, a combination of the X-ray conditions, the reconstruction range, the weight setting conditions, the imaging condition setting conditions, the imaging/image conditions, the reconstruction filter, the projection data correction method, and the projection data range received in the imaging condition reception screen 400 may be stored in the HDD device 115. In this case, at the time of next imaging under the same conditions, the imaging condition input unit 211 reads and uses the combination from the HDD device 115 according to an instruction from the user. In this case, it is not necessary for the user to input the X-ray conditions or the like at every imaging. Further, a plurality of combinations of the above setting conditions may be stored in the HDD device 115 in advance and the user may select one from the plurality of combinations.

[Iterative Correction Process]

Next, the iterative correction process by the iterative reconstructing unit 233 of the present embodiment will be described with reference to FIGS. 4 and 5.

As described above, in the present embodiment, the noise reduction rate or the X-ray dose reduction rate designated (desired) in the actual imaging conditions is converted into the noise reduction rate or the X-ray dose reduction rate in the representative imaging conditions and the iterative correction parameter corresponding to the reduction rate is used for the iterative correction. When the mode of the fixed noise value is selected, the noise value in the corresponding range in the initial image is measured and the noise reduction rate or the X-ray dose reduction rate designated (desired) in the actual imaging conditions is calculated from the ratio of the measured noise value to a desired fixed noise value. Then, the iterative correction parameter corresponding to the reduction rate is used for the iterative correction.

Among the imaging conditions, the imaging conditions that affect the iterative correction parameter include the reconstruction filter received through the reconfiguration filter setting area 460, the measured projection data correction method received through the projection data correction setting area 470, and the measured projection data range used for the iterative correction received through the projection data range setting area 480, among the imaging conditions set through the imaging condition reception screen 400 of FIG. 3.

Hereinafter, in the present embodiment, a conversion method when the imaging conditions (actual imaging conditions) set by the user and the representative imaging conditions have different reconstruction filters will be described.

As described above, the iterative reconstructing unit 233 first makes projection calculation in the forward direction (hereinafter, referred to as forward projection calculation) for the initial image to obtain the calculated projection data. A final CT image is obtained by making the iterative correction on the initial image so that the obtained calculated projection data and the measured projection data are equalized. As the iterative correction parameter used for the iterative correction, optimal values corresponding to different weights for different pixel positions are used. This iterative correction parameter is calculated by converting a parameter (reference parameter) optimized in the representative imaging conditions (representative imaging condition) into an optimal value in the imaging conditions at the time of imaging.

Note that the iterative correction parameter is a parameter used for the iterative correction in order to calculate a CT image that achieves a desired noise reduction rate or an X-ray dose reduction rate.

To this end, as illustrated in FIG. 4, the iterative reconstructing unit 233 of the present embodiment includes a table unit 310 that holds the relationship between the noise reduction rate and the iterative correction parameter in the representative imaging conditions and holds a weight serving as a reference for image in the representative imaging conditions, a parameter determining unit 320 that determines an iterative correction parameter to be used for the iterative correction for each pixel in accordance with the imaging conditions received at the time of actual imaging, and an iterative correcting unit 330 that iteratively corrects the initial image using the determined iterative correction parameter.

[Noise Reduction Rate and X-Ray Dose Reduction Rate]

Prior to describing the above units, the noise reduction rate and the X-ray dose reduction rate will first be described.

In the present embodiment, the noise reduction rate is indicated by a percentage of reduction of a noise of the CT image after the iterative correction with respect to the noise of the initial image reconstructed by using the analytical reconstruction method such as a known Feldkamp method, for example, as expressed by the following equation (1).

[Equation 1]

$$\text{Noise reduction rate [\%]} = \left(1 - \frac{\text{Sequentially-corrected image noise}}{\text{Initial image noise}}\right) \cdot 100 \quad (1)$$

In the meantime, in the present embodiment, the X-ray dose reduction rate is indicated by a percentage of reduction of an X-ray dose that may be reduced by iterative reconstruction under the conditions of acquiring the same image quality as the CT image reconstructed using the above analytical reconstruction method. In the present embodiment, the image quality is described using the standard deviation SD indicating a noise in an arbitrary region, but another evaluation index such as a spatial resolution may be used. Since the X-ray dose reduction rate may be expressed by the following equation (2) since the X-ray dose may be approximated from SD.

[Equation 2]

$$\text{X-ray dose reduction rate [\%]} = \left\{1 - \left(\frac{\text{Sequentially-corrected image noise}}{\text{Initial image noise}}\right)^2\right\} \cdot 100 \quad (2)$$

Thereafter, since the noise reduction rate and the X-ray dose reduction rate may be converted from the equations (1) and (2), the description of the X-ray dose reduction rate is omitted and the noise reduction rate will be described as a representative.

[Table Unit]

For the CT image (initial image) acquired in the representative imaging conditions, the table unit 310 stores the relationship between the noise or X-ray dose reduction rate obtained by the iterative correction and a reference parameter used for the iterative correction. For example, the relationship between the reduction rate and the reference parameter is created in advance as a function of the reference parameter having the noise reduction rate as a variable and is held in the memory 132 or the HDD device 134. Hereinafter, in the present specification, a function indicating the relationship between the noise reduction rate and the reference parameter is called a table.

In addition, weight images calculated from the weight for each detection element have different weight values for different pixel positions. Therefore, optimal iterative correction parameters for obtaining images of desired image quality (noise reduction rate, spatial resolution, etc.) are different depending on not only the imaging conditions but also the pixel positions on the images. The table unit 310 of the present embodiment calculates and holds the weight of the reference position (referred to as a reference weight) in order to determine an optimal iterative parameter for each pixel position.

To this end, the table unit 310 of the present embodiment includes a table calculating unit 311, a reference weight calculating unit 312 and a calculation table storage unit 313, as illustrated in FIG. 4. These units are realized by the CPU 133 executing a program but some thereof are built on a storage unit constituted by the memory 132 and the HDD device 134.

[Table Calculating Unit]

The table calculating unit 311 creates a function (table) for specifying the relationship between the size of the reference parameter and the noise reduction rate of the CT image using the representative phantom acquired in advance (step S1101 in FIG. 5). The table is calculated by actually using the results of iterative correction on the CT image (initial image) of the phantom. At this time, this CT image is acquired under the representative imaging conditions.

The table calculating unit 311 iteratively corrects the obtained initial image by using a plurality of reference parameters $\beta_b$ which are different iterative correction parameters. Then, the initial image noise and the iteratively-corrected CT image noise are measured to calculate the noise reduction rate for each reference parameter $\beta_b$. The noise measurement is performed within a preset ROI.

Noise and the ROI for measuring the weight are set at the position of the CT image rotation center of the X-ray CT apparatus 100. However, the position of the ROI is not limited thereto. The ROI may be set at a position in the periphery of the CT image rotation center. Further, a plurality of ROIs may be set at positions in the periphery other than the CT image rotation center. At this time, noise may be measured for each ROI to create a table, or the table may be created by averaging measured values of noise of a plurality of ROIs.

Figure 6B:
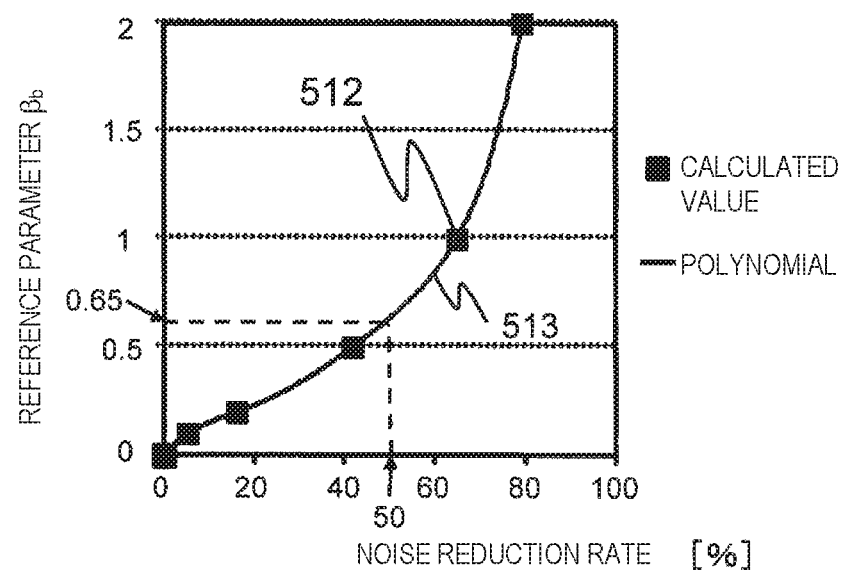
FIG. 6B is a graph for explaining an example of change in noise reduction rate for each reference parameter of the first embodiment.

The processing of the table calculating unit 311 will be described with reference to (a) of FIG. 6. (a) of FIG. 6 illustrates a CT image 510 of a tomographic plane obtained by imaging a cylindrical phantom with a diameter of 30 cm and a height of 100 cm filled with water, under the representative imaging conditions. As described above, an ROI 511 for measuring a noise is set at the rotation center of the CT image 510.

First, the table calculating unit 311 measures the noise in the ROI 511 of the initial image. Thereafter, while changing the value of the reference parameter $\beta_b$, the iterative correcting process is performed and the noise of the ROI 511 of the corrected CT image is measured. Then, the noise reduction rate is calculated according to the equation (1).

An example of the change in the noise reduction rate for each value of the reference parameter $\beta_b$ at this time is illustrated in (b) of FIG. 6. In the figure, reference numeral 512 denotes a measured value obtained by plotting a noise reduction rate for each value of each reference parameter $\beta_b$.

The table calculating unit 311 calculates an approximate curve 513 from the plot result of the measured value 512, for example, using the least squares method or the like. A function representing the approximate curve 513 representing the relationship between the value of the reference parameter $\beta_b$ and the noise reduction rate is held as a table. This table may be used to obtain the reference parameter $\beta_b$ that implements an arbitrary noise reduction rate.

In addition, as described above, the iterative correction repeats the first calculation and the second calculation. The number of repetitions is predetermined. Even with the same iterative correction parameter, the noise reduction rate is varied depending on the number of repetitions. Therefore, the table calculating unit 311 may create the table every repetition, for example.

FIG. 7 illustrates an example of the table created by the table calculating unit 311 in the above-described procedure. Here, an example of table made for each of the number of times repetition (iteration) will be described. A database holding the table for each of the number of times repetition is called a parameter table. As illustrated in this figure, the parameter table 710 holds a table 713 for each of the number of times repetition (iteration) 711. At this time, the imaging conditions (in this embodiment, the type of reconstruction filter) 712 used as the representative imaging conditions may also be held.

Although the case where the parameter table 710 is created by using the CT image acquired actually by the X-ray CT apparatus 100 has been described here as an example, the method of creating the parameter table 710 is not limited thereto. The parameter table 710 may be created using simulation data by a virtual X-ray CT apparatus.

[Reference Weight Calculating Unit]

The reference weight calculating unit 312 calculates a weight value of a pixel in an area (reference area) that is a predetermined reference on the CT image, as a reference weight, based on the weight for each detection element. Specifically, according to the conditions of FOV and its center position which may be designated by the user as the imaging conditions, the reference weight calculating unit 312 calculates a weight distribution (weight image) $W_I$ (j) from the weight W (i) of each detection element to obtain the weight Wb of the reference area (hereinafter, referred to as a reference weight) (step S1102 in FIG. 5).

The weight for each detection element is set in advance through the weight setting area 430 of the imaging condition reception screen 400. The weight image $W_I$ (j) is a distribution of weight values for each pixel obtained by performing a simple reverse projection process, which does not include a known reconstruction filter process, on the weight W (i) of the detection element.

For example, if an FOV which may be designated by the user has three types of FOVs of 300, 500 and 700 [mm] and two types of FOV center positions of X=Y=Z=0 [mm] and X=30 [mm], and Y=Z=0 [mm], a total of six reference weights Wb are acquired.

The reference area may be at the same position as the ROI 511 used for noise measurement in the table calculating unit 311. A plurality of ROIs located in the periphery other than the center position may be used.

The process of the reference weight calculating unit 312 will be described with a specific example with reference to (a) and (b) of FIG. 8.

Figure 8A:
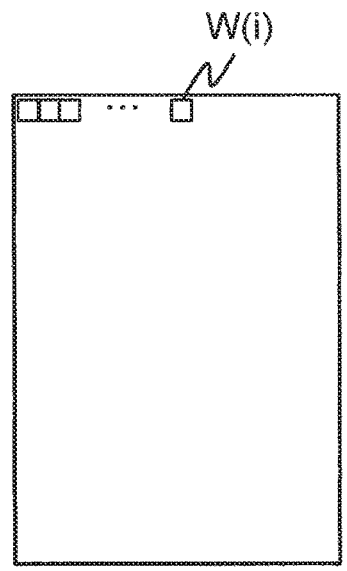
FIG. 8A is an explanatory view for explaining a weight of a detection element of the first embodiment.
Figure 8B:
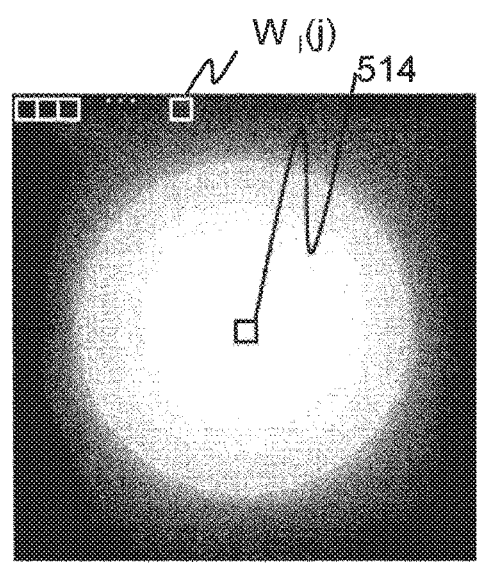
FIG. 8B is an explanatory for explaining a result of calculation by a reference weight calculating unit.

(a) of FIG. 8 shows a distribution of the weight W (i) of a detection element. Here, i denotes a detection element number assigned to each detection element for each projection angle. When projection angles are different, even in the detection elements of the same channel and column, separate detection element numbers are set. Here, a weight W (i) distribution in case where a constant value is selected in the weight setting area 430 of the imaging condition reception screen 400 is illustrated. That is, the values of the respective weights W (i) are all the same value. The value of the weight W (i) is, for example, 1. The value of the weight W (i) may be a value other than 1.

(b) of FIG. 8 is a weight image $W_I$ (j) created from the detection element weight W (i) distribution illustrated in (a) of FIG. 8. Here, the weight image $W_I$ (j) of the CT image obtained when the FOV is 700 [mm] and the center position of the FOV is designated as X=Y=Z=0 [mm] is illustrated. The weight image $W_I$ (j) is obtained by applying the same process as the CT image reconstruction to the weight W (i) of each detection element. Here, j denotes a pixel number.

As illustrated in (a) of FIG. 8, since the value of the weight W (i) of each detection element is a constant value, the weight image $W_I$ (j) has a substantially constant pixel value in a circular shape near the image center. In addition, since the periphery of the image is outside the field of view, the weight image $W_I$ (j) has a value close to 0.

The reference weight calculating unit 312 calculates the weight value $W_I$ (j) of a pixel j in the reference area (ROI 514) by using the following equation (3). The weight $W_I$ (j) of the pixel j is a result of calculation of the weight image of a pixel in the ROI 514 of (b) of FIG. 8.

[Equation 3]

$$W_I(j) = \sum_{i=1}^{I} W(i)C(i,j) \sum_{l=1}^{L} C(i,l) \quad (3)$$

Here, I represents the total number of detection element numbers different for each projection angle, L represents the total number of pixels, and 1 represents the numbers of L pixels on a line connecting the pixel j which is iteration object and the detection element i. C (i, j) represents the proportion of the pixel j contributing to the detection element i, which is varied depending on the position of the X-ray detecting unit 122, a forward projection calculation method or the reverse projection calculation method.

Then, the reference weight calculating unit 312 calculates the reference weight Wb from the weight $W_I$ (j) of each pixel j in the ROI 514. For example, the reference weight Wb is obtained by calculating the average of the weights $W_I$ (j) of each pixel j. The reference weight Wb is not limited to the average value but may be the maximum value, the minimum value, and the like of $W_I$ (j).

[Calculation Table Storage Unit]

The calculation table storage unit 313 stores the table 713 calculated by the table calculating unit 311 and the reference weight Wb calculated by the reference weight calculating unit 312 in the memory 132, the HDD device 134, and the like. The stored table 713 and reference weight Wb are referred to by the parameter determining unit 320.

The process of the table unit 310 is performed before imaging the subject 101 or may be performed before shipment of the X-ray CT apparatus 100.

Further, in the present embodiment, as illustrated in FIG. 7, the table 713 is acquired for each of the number of times of repetition (here, 20 times, 60 times, . . . ) 711 which may actually be used for the iterative correction. However, without being limited thereto, the table 713 may be acquired with two or more different number of repetition (iteration) times 711. In this case, the table of different number of repetition times is obtained by known linear interpolation or extrapolation based on the acquired table 713 of repetition times. Thereby, the number of tables 713 to be stored may be reduced.

In the present embodiment, as illustrated in FIG. 7, the reconstruction filter 712 of the representative imaging conditions is used to determine a function associating the reference parameter and the noise reduction rate, as the table 713, for each of the number of the repetition (iteration) times 711. However, the representative imaging conditions are not limited thereto. A table (an approximate curve associating the reference parameter and the noise reduction rate) may be acquired for other imaging conditions or reconstruction conditions, such as a tube voltage and an operating speed of the bed. Here, the number of times of iteration refers to the number of times of repetition of iterative correction.

In the present embodiment, a plurality of calculation tables may be stored depending on the imaging conditions such as the tube voltage, the reconstruction conditions such as FOV, and the type of measured projection data. As a result, an error may be reduced from the true value of the iterative correction parameter due to a difference in the conditions.

[Parameter Determining Unit]

The parameter determining unit 320 converts the desired reduction rate in the actual imaging conditions, which is the imaging conditions at the time of actual imaging, into the representative reduction rate that is the reduction rate in the representative imaging conditions, and determines an iterative correction parameter that implements the desired reduction rate by referring to the relationship (table) stored in the table unit 310. The actual imaging conditions are received in the imaging condition reception screen 400.

That is, the parameter determining unit 320 determines, as the actual imaging conditions, an iterative correction parameter that implements the noise reduction rate (actual reduction rate) received through the imaging/image setting area 450 of the imaging condition reception screen 400 under the imaging conditions received in the imaging condition reception screen 400. At this time, the parameter determining unit 320 converts the actual reduction rate into the noise reduction rate (representative reduction rate) of the representative imaging conditions to obtain the iterative correction parameter according to the table 713.

To this end, as illustrated in FIG. 4, the parameter determining unit 320 of the present embodiment includes a representative noise reduction rate converting unit 321 for converting the desired reduction rate (actual noise reduction rate) set as the imaging conditions into a representative noise reduction rate, a calculation table referring unit 322 for referring to the relationship (table) stored in the table unit 310 to determine the reference parameter $\beta_b$ corresponding to the representative noise reduction rate, a weight calculating unit 323 for calculating the weight of each position (pixel) of the CT image based on the weight of each detection element, and a parameter converting unit 324 for performing conversion into the parameter of each position using the reference parameter $\beta_b$ and the weight of each position.

Hereinafter, details of processing of each part of the parameter determining unit 320 of the present embodiment will be described with reference to FIG. 5.

[Representative Noise Reduction Rate Converting Unit]

The representative noise reduction rate converting unit 321 uses a noise increase/decrease ratio, which is a ratio of the noise of the CT image acquired in the representative imaging conditions to the noise of the CT image acquired in the actual imaging conditions by a difference between the representative imaging conditions and the actual imaging conditions, to convert the desired reduction rate (actual noise reduction rate) set as the imaging conditions into a noise reduction rate (representative reduction rate) to be input to the table 713 of the representative imaging conditions (steps S1201 and S1202 in FIG. 5). Details of the conversion process will be described below.

Prior to describing the conversion process, the relationship between the number of times of repetition (iteration) and the noise (SD) will be described. This relationship is illustrated in (a) of FIG. 9. (a) of FIG. 9 is a graph illustrating how the noise (SD) 531 is changed with the increase in the number of times of repetition (iteration), with a horizontal axis representing the number of times of repetition (iteration) and a vertical axis representing the noise (SD).

As illustrated in the figure, the noise (SD) decreases with the increase in the number of times of repetition (iteration) and finally converges to a predetermined value 534. (a) of FIG. 9 exemplifies a case where the noise SD 531 enters the convergence stage where it is not changed when the number of times of repetition (iteration) exceeds 60. The number of times of repetition (iteration) of 0 means the initial image.

In the present embodiment, when the same iterative correction parameter is used, the noises at the convergence stage of the iterative correction are same regardless of the noise of the initial image.

First, the representative noise reduction rate converting unit 321 uses a noise (532 in (a) of FIG. 9) of the CT image (initial image) acquired by the reconstruction filter of the actual imaging conditions to calculate a noise (533 in (a) of FIG. 9) of the CT image (initial image) acquired as the representative imaging conditions (step S1201).

Here, the representative noise reduction rate converting unit 321 first calculates the noise (SDAint) 532 of the initial image acquired by the reconstruction filter of the actual imaging conditions. The calculation is performed by using a pixel value of the initial image actually obtained. Then, the actual reduction rate (RRA %) set in the imaging/image setting area 450 is used to calculate an iteratively-corrected target noise (SDAtar). The target noise (SDAtar) may be calculated by the following equation (4).

$$SDAtar=SDAint\times(100-RRA)/100 \qquad (4)$$

Next, the representative noise reduction rate converting unit 321 calculates a noise increase/decrease ratio which is a ratio of the noise of the CT image acquired in the representative imaging conditions to the noise of the CT image acquired in the actual imaging conditions, as expressed by the following equation (5).

[Equation 5]

$$\text{Noise increase/decrease ratio} = \frac{CT \text{ image noise of representative imaging conditions}}{CT \text{ image noise of actual imaging conditions}} \qquad (5)$$

In the present embodiment, the actual imaging conditions and the representative imaging conditions are different from each other in terms of only the reconstruction filter. Therefore, a noise difference between both images is due to the reconstruction filter. In the present embodiment, a filter noise table 520 holding the noise (SD) 522 is prepared for each type of reconstruction filter 521, as illustrated in (b) of FIG. 9, the noise ratio between filters is calculated as the noise increase/decrease ratio.

The filter noise table 520 stores the noise of the CT image when the same subject is imaged under the representative imaging conditions for each reconstruction filter that is supposed to be used. Here, for each reconstruction filter, a representative phantom is used to image the subject under the representative imaging conditions, the SD is measured, and results of the measurement are stored. (b) of FIG. 9 exemplifies a case where abdomen, head, thoracic lung field, Ramp, and Shepp-logan are held as the type 521 of the reconstruction filter that is supposed to be used. As illustrated in the figure, the filter noise table 520 is created in advance and is held in the HDD device 134 or the like.

The representative noise reduction rate converting unit 321 refers to the filter noise table 520 to convert a desired reduction rate (actual reduction rate) into the representative reduction rate. That is, the representative noise reduction rate converting unit 321 calculates an inter-filter noise ratio (SDRfil/SDAfil) of the noise (SDRfil) by the reconstruction filter of the representative imaging conditions to the noise (SDAfil) by the reconstruction filter of the actual imaging conditions, as the noise increase/decrease ratio (RSD).

For example, when the type 521 of the reconstruction filter of the representative imaging conditions is Ramp and the type 521 of the reconstruction filter of the actual imaging conditions is for the head, the inter-filter noise ratio calculated using the value of the filter noise table 520 is 0.5 (=20/40).

Then, using the noise increase/decrease ratio (RSD), the representative noise reduction rate converting unit 321 calculates the noise (SDRint) of the initial image acquired under the representative imaging conditions from the relationship of the equation (5). The noise (SDRint) of the initial image acquired under the representative imaging conditions may be calculated by the following equation (6).

$$SDRint=RSD\times SDAint \qquad (6)$$

Next, the representative noise reduction rate converting unit 321 uses the noise (SDRint) of the initial image acquired under the representative imaging conditions and the target noise (SDAtar) to calculate the noise reduction rate (representative noise reduction rate RRR %) in the representative imaging conditions (step S1202).

The representative noise reduction rate (RRR) may be calculated by the following equation (7).

$$RRR=(1-SDAtar/SDRint)\times100 \qquad (7)$$

In the above description, the representative noise reduction rate converting unit 321 calculates the noise (SDRint) when the initial image is acquired under the representative imaging conditions, from the noise (SDAint) of the initial image calculated under the actual imaging conditions, and calculates the representative reduction rate (RRR) from the target noise (SDAtar). However, the present invention is not limited to this method.

For example, the representative noise reduction rate RRR may be calculated according to the following equation (8) using the noise reduction rate (actual noise reduction rate) and the noise increase/decrease ratio set through the imaging/image setting area 450 as the actual imaging conditions.

[Equation 8]

$$\text{Representative noise reduction rate [\%]} = \left(1 - \frac{\left(1 - \frac{\text{Actual noise reduction rate}}{100}\right)}{\text{Noise increase/decrease ratio}}\right) \cdot 100 \quad (8)$$

As described above, the noise increase/decrease ratio may be calculated from the filter noise table 520. Therefore, as described above, it is not always necessary to calculate the noise (SDAint) of the initial image of the actual imaging conditions or the noise (SDRint) of the initial image of the representative imaging conditions, but the representative noise reduction rate may be calculated directly according to the equation (8).

For example, when the real noise reduction rate is 75%, the type 521 of the reconstruction filter of the representative imaging conditions is Ramp, and the type 521 of the reconstruction filter of the actual imaging conditions is for the head, the representative noise reduction rate is 50%=(1−(1−75/100)/0.5)×100).

[Calculation Table Referring Unit]

The calculation table referring unit 322 extracts the reference parameter $\beta_b$ corresponding to the representative noise reduction rate obtained by converting the actual noise reduction rate, from the relationship (table) stored in the table unit 310, and determines the iterative correction parameter (step S1203 in FIG. 5).

Specifically, the calculation table referring unit 322 determines the reference parameter $\beta_b$ corresponding to the representative noise reduction rate according to the table 713 created by the table calculating unit 311 of the table unit 310.

For example, in the parameter table 710 of FIG. 7, it is assumed that the approximate curve of the table 713 in which the number of the iteration times 711 is 60 indicates the change form of (b) of FIG. 6. For example, when the representative noise reduction rate is calculated to be 50%, the calculation table referring unit 322 obtains 0.65 as the reference parameter $\beta_b$ according to the approximation curve 513.

[Weight Calculating Unit]

The weight calculating unit 323 calculates the weight $W_I$ (j) for each pixel on the CT image based on the weight W (i) for each detection element (step S1204 in FIG. 5). The calculation method of the weight image $W_I$(j) is the same as the calculation method by the reference weight calculating unit 312. However, the reference weight calculating unit 312 calculates the weight value only for the reference area portion, whereas the weight calculating unit 323 calculates the weight value of the entire area in the image.

Therefore, for example, when the reference weight calculating unit 312 calculates the reference weight, the weight value calculating unit 312 may calculate the weight value of the entire area and stores it in the memory 132 or the like and the weight calculating unit 323 may read the weight value from the memory 132 or the like.

Figure 10A:
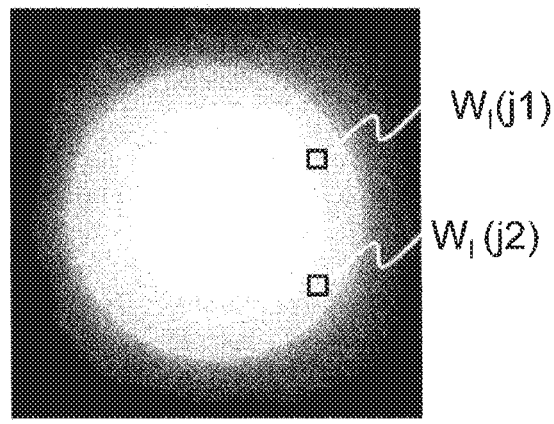
FIG. 10A is an explanatory view for explaining an example of a weight image of the first embodiment.
Figure 10B:
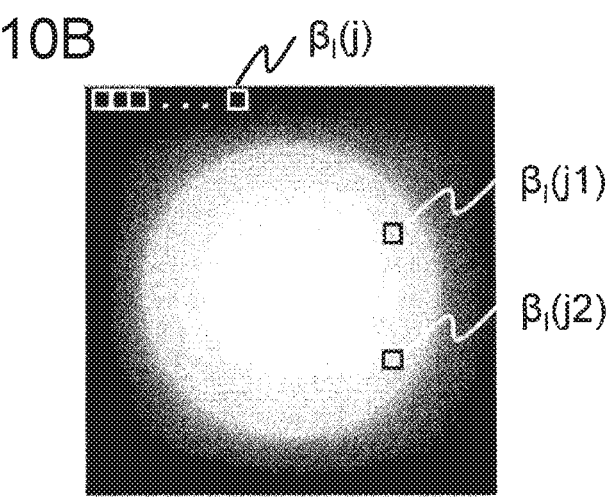
FIG. 10B is an explanatory view for explaining an example of an iterative correction parameter at each pixel position of the first embodiment.

(a) of FIG. 10 shows the calculated weight image $W_I$ (j). The weight image $W_I$(j) is an image whose pixel value is the weight value of each position (pixel) of the CT image. j denotes the pixel number. As described above, in the present embodiment, the value of the weight W (i) of each detection element is constant. Since the weight image $W_I$(j) is created from this weight W (i) distribution, the pixel values ($W_I$(j1) and $W_I$ (j2)) are different at respective pixel positions (e.g., j1 and j2).

[Parameter Converting Unit]

The parameter converting unit 324 determines an iterative correction parameter $\beta_I$(j) for each pixel from the weight $W_I$ (j) for each pixel j and the reference parameter $\beta_b$.

The parameter converting unit 324 uses the reference weight Wb calculated by the reference weight calculating unit 312, the reference parameter $\beta_b$ specified by the calculation table referring unit 322, and the weight image $W_I$ (j) calculated by the weight calculating unit 323 to calculate an iterative correction parameter distribution $\beta_I$(j) of each pixel position j according to the following equation (9).

[Equation 9]

$$\beta_I(j) = \beta_b \cdot \frac{W_I(j)}{W_b} \quad (9)$$

As described above, the reference weight Wb is calculated under the same conditions as FOV and the center position of the FOV designated in the imaging conditions.

(b) of FIG. 10 illustrates the iterative correction parameter distribution $\beta_I$ (j) of each pixel position j calculated by the parameter converting unit 324. Since the pixel values ($W_I$ (j1) and $W_I$ (j2)) are different at respective pixel positions (e.g., j1 and j2), the values ($\beta_I$ (j1) and $\beta_I$ (j2)) of the parameter $\beta$ are also different.

[Iterative Correcting Unit]

The iterative correcting unit 330 uses the iterative correction parameter $\beta_I$ (j) calculated by the parameter determining unit 320 to perform an iterative correction (iterative reconfiguration) process (step S1300 in FIG. 5). In the present embodiment, the iterative correcting unit 330 performs iterative correction for each pixel j by applying the iterative correction parameter $\beta_I$ (j) for each pixel j.

The iterative correcting unit 330 iteratively corrects the CT image so that the calculated projection data obtained by the forward projection of the CT image by calculation and the measured projection data approach each other. At this time, the CT image is iteratively corrected using the iterative correction parameter $\beta_I$ (j) (iterative correction parameter distribution $\beta_I$ (j) of each pixel position j calculated by the parameter determining unit 320, as the iterative correction parameter. As a result, a CT image from which noise is removed with high precision is generated.

As an algorithm for correcting an image, a known iterative reconstruction method may be used. Here, as an example, a case of using SPS (a Separable-Paraboloidal-Surrogate) method will be described.

To this end, the iterative correcting unit 330 includes an analytical reconstructing unit 331, a forward projecting unit 332, a differentiating unit 333, a reverse projection processing unit 334, a Prior calculating unit 335 and an image correcting unit 336. Hereinafter, processing of each part in the iterative correction processing step S1300 will be described with reference to FIG. 11.

The analytical reconstructing unit 331 uses an analytical reconstruction technique such as the known Feldkamp method to obtain a CT image $\lambda^{k=0}$ (j) from the measured projection data R (i) corrected by the correction processing unit 232 (step S1301). Here, k is an integer of 0 or more indicating the number of times of repetition of iterative reconstruction (the number of times of iteration or the number of times of correction), and k=0 represents the initial image. j is the pixel number, and $\lambda^k$ (j) represents a pixel value of the pixel j of an image having the iteration times k.

In the SPS method, a CT image $\lambda^{k+1}$ (j) whose number of times of correction is (k+1) is expressed by the following equation (10) using the CT image $\lambda^k$ (j) at k times.

[Equation 10]

$$\lambda^{k+1}(j) = \lambda^k(j) - \frac{\sum_{i=1}^{I} W(i)C(i,j)\left(R(i) - \sum_{l=1}^{L} C(i,l)\lambda^k(l)\right) + P1}{\sum_{i=1}^{I} W(i)C(i,j)\sum_{l=1}^{L} C(i,l) + P2} \quad (10)$$

Where, j is the total number of pixels. i represents a detection element number and I represents the total number of detection elements. W (i) is the weight of each detection element. P1 and P2 represent calculation equations of the numerator and denominator, respectively.

This iterative reconstruction method is applicable not only to general two-dimensional (x and y directions) tomographic images but also to one-dimensional data (x direction), three-dimensional data (x, y and z directions) obtained by superimposing images in the body axis direction z, and four-dimensional data (x, y, z and t) in consideration of time direction t. The pixel number j represents a pixel to be calculated in the iterative reconstruction process. For example, in the case of two-dimensional data, the range of the pixel number j is (1×1), (2×1), . . . , (X×1), (1×2), . . . , (X×Y). X and Y represent the numbers of pixels in the x and y directions, respectively.

Hereinafter, the iterative reconstruction process according to the equation (10), that is, a process of correcting the CT image $\lambda^k$ (j) with the correction times k and calculating the CT image $\lambda^{k+1}$ (j) with the correction times (k+1), will be described for each step.

The iterative correcting unit 330 performs the following process until the number of times of repetition (the number of times of iteration) reaches a predetermined number of times (steps S1302 and S1307).

The forward projecting unit 332 performs a forward projection process on the pixels of the CT image $\lambda^k$ (j) to obtain calculated projection data S (i) (step S1303). The calculated projection data S (i) is obtained by calculating the following equation (11).

[Equation 11]

$$S(i) = \sum_{l=1}^{L} C(i,l)\lambda^k(l) \quad (11)$$

In the equation (11), l represents the number of L pixels on a line connecting the pixel j which is correction object and the i-th detection element (detection element i). C (i, l) represents the proportion of the pixel l contributing to the detection element i, which is varied depending on the position of a detection element, the forward projection calculation method or the reverse projection calculation method.

The differentiating unit 333 subtracts the calculated projection data S (i) from the measured projection data R (i) according to the following expression (12) to obtain corrected projection data ΔRk(i) (step S1304).

[Equation 12]

$$\Delta R^k(i) = R(i) - \sum_{l=1}^{L} C(i,l)\lambda^k(l) \quad (12)$$

The Prior calculating unit 335 calculates P1 and P2 according to the following equations (13) and (14), respectively. Here, $\Psi$ represents the first derivative of the known Generalized-Geman-Prior. P1 and P2 are equations using known Surrogate Function.

[Equation 13]

$$P1 = \beta \sum_{m \in N_j} d_{jm} \Psi(\lambda_j^k - \lambda_m^k) \quad (13)$$

$$P2 = \beta \sum_{m \in N_j} d_{jm} \frac{\Psi(\lambda_j^k - \lambda_m^k)}{\lambda_j^k - \lambda_m^k} \quad (14)$$

At this time, the Prior calculating unit 335 multiplies a difference in CT value between pixels constituting the CT image by the iterative correction parameter and then adds it to the corrected image after Likelihood calculation. This process may reduce the difference in CT value between pixels during the iterative correction, thereby achieving the effect of reducing noise.

In the above equations (13) and (14), β is a fixed iterative correction parameter (iterative correction parameter) indicating the intensity of Prior. In the present embodiment, instead of β, the iterative correction parameter $\beta_I$ (j) for each pixel j calculated by the parameter determining unit 320 is used. In addition, $(\lambda_j^k - \lambda_m^k)$ is a function with a difference $(\lambda_j^k - \lambda_m^k)$ in CT value between two pixels in the CT image $\lambda^k$ (j) as a variable.

The reverse projection processing unit 334 performs the reverse projection process on the corrected projection data $\Delta R^k$ (i) according to the following equation (15) to generate a corrected image $\Delta\lambda^k$ (j) (step S1305).

[Equation 15]

$$\Delta\lambda^k(j) = \frac{\sum_{i=1}^{I} W(i)C(i,j)\Delta R^k(i) + P1}{\sum_{i=1}^{I} W(i)C(i,j)\sum_{l=1}^{L} C(i,l) + P2} \quad (15)$$

The image correcting unit 336 uses the corrected image $\Delta\lambda^k$ (j) to obtain the corrected CT image $\lambda^{k+1}$ (j) by calculating the following equation (16), and obtains an image of the repetition (iteration) times (k+1) (step S1306).

[Equation 16]

$$\lambda^{k+1}(j) = \lambda^k(j) - \Delta\lambda^k(j) \quad (16)$$

Upon obtaining the image of the repetition (iteration) times (k+1), the iterative correcting unit 330 increments the correction times k by 1 (step S1307) and proceeds to step S1302 in which the process is repeated from the process (step S1303) of the analytical reconstructing unit 331 until the correction times k after the increment becomes equal to the preset correction times K (step S1302). As a result, the processing by each of the above units is repeated until the correction times k after the increment becomes equal to the preset correction times K.

When the correction times k reaches K, the image display unit 234 displays the obtained CT image $\lambda^k$ (j) on the monitor 135.

As described above, the X-ray CT apparatus 100 of the present embodiment includes the X-ray generating unit 121 that generates an X-ray according to the set imaging conditions, the X-ray detecting unit 122 that detects the X-ray passed through the subject 101 with a plurality of detection elements to obtain the measured projection data, and the image generating unit 130 including the iterative reconstructing unit 233 that performs the iterative correction on the CT image so that the calculated projection data obtained by the forward projection calculation from the CT image generated from the measured projection data becomes equal to the measured projection data. The iterative reconstructing unit 233 includes the table unit 310 that stores, as a table, the relationship between the reduction rate, which is a ratio at which the noise or the X-ray dose is reduced by the iterative correction, for the CT image acquired under the representative imaging conditions, and the reference parameter which is a parameter used for the iterative correction to realize the reduction rate, the parameter determining unit 320 that converts the reduction rate desired in the actual imaging conditions, which are imaging conditions at the time of actual imaging, into the representative reduction rate which is the reduction rate in the representative imaging conditions, and refers to the relationship stored in the table unit 310 to determine the iterative correction parameter to implement the desired reduction rate, and the iterative correcting unit 330 that uses the iterative correction parameter determined by the parameter determining unit 320 to perform the iterative correction.

The parameter determining unit 320 may include the representative noise reduction rate converting unit 321 that converts the desired reduction rate into the representative reduction rate by using a noise increase/decrease ratio, which is a ratio of the noise of the CT image acquired under the representative imaging conditions to the noise of the CT image acquired under the actual imaging conditions due to the difference between the representative imaging conditions and the actual imaging conditions, the calculation table referring unit 322 that extracts the reference parameter corresponding to the converted representative reduction rate from the table, the weight calculating unit 323 that calculates the weight for each pixel on the CT image based on the weight for each detection element, and the parameter converting unit 324 that determines the iterative correction parameter for each pixel from the weight for each pixel and the reference parameter.

Further, the table unit 310 may further include the reference weight calculating unit 312 that calculates a weight value of a pixel in a predetermined reference area on the CT image as a reference weight based on the weight of each detection element, and the parameter converting unit 324 may further use the reference weight to determine the iterative correction parameter for each pixel.

The imaging conditions set by the user and the representative imaging conditions have different reconstruction filters, the iterative reconstructing unit 233 may further include the filter noise table 520 that stores the noise of the CT image at the time of imaging the same subject under the representative imaging conditions, for each of the reconstruction filters, and the representative noise reduction rate converting unit 321 may refer to the filter noise table 520 to convert the desired reduction rate into the representative reduction rate.

In this manner, according to the present embodiment, the reduction rate of the actual imaging conditions is converted into the reduction rate of the representative imaging conditions to obtain the optimal iterative correction parameter in the actual imaging conditions. Therefore, it is unnecessary to hold the optimal iterative correction parameter for each of the imaging conditions, but the optimal iterative correction parameter may be held only for the representative imaging conditions. Therefore, according to the present embodiment, the optimal iterative correction parameters in the actual imaging conditions may be obtained without increasing the number of man-days and the number of tables required for table creation.

Further, in the present embodiment, the reference weight Wb calculated in advance is used to determine the iterative correction parameter $\beta_I$ (j) according to the weight of each position. As a result, since the iterative correcting unit 330 may determine a parameter after the Prior calculation at each position, a CT image may be acquired that achieves a desired noise reduction rate regardless of an area of the CT image. That is, the iterative correcting unit 330 may iteratively correct the CT image using the optimal iterative correction parameter $\beta_I$ (j) for each pixel.

As a result, the image generating unit 130 of the present embodiment may generate a CT image from which noise has been removed with high accuracy. Since this CT image is generated by the iterative reconstruction, the calculated projection data projecting this CT image matches well with the measured projection data, thereby making it possible to achieve a CT image obtained by imaging the measured projection data with high accuracy.

Further, in the present embodiment, paying attention to the fact that the noise reduction effect depends on the measured projection data and a set value of the iterative correction parameter, a parameter of each position of the CT image is calculated and used from a table calculated in advance. Thereby, the optimal iterative correction parameter $\beta_I$ (j) determined according to the desired noise reduction rate, the imaging conditions, the reconstruction conditions, and the measured projection data may be easily introduced without greatly changing the iterative correction process itself.

As explained above, the X-ray CT apparatus 100 of the present embodiment uses the optimal iterative correction parameter for each pixel in the iterative reconstruction (iterative correction). Therefore, reconstruction may be performed by using optimal iterative correction parameters corresponding to different weights for different pixels. Therefore, the image quality may be controlled with high accuracy, thereby obtaining a high quality CT image which achieves a desired noise reduction rate.

In addition, in the present embodiment, with respect to the reconstruction filter, the iterative correction parameter optimal for each pixel is held in association with only the representative imaging conditions. Then, at the time of actual imaging, the iterative correction parameter is converted into a value for the actual imaging conditions. Therefore, memory capacity may also be saved.

In the present embodiment, the case where the CT image is reconstructed by using the measured projection data for one round of 360 degrees has been described by way of example. However, the present invention is not limited thereto. The CT reconstruction method may be, for example, a known half reconstruction or a reconstruction using the measured projection data for one around of 360 degrees or more.

Examples

In order to verify the effectiveness of this embodiment, a cylindrical phantom with a diameter of 38 cm and a height of 100 cm filled with water was imaged. The phantom was installed at the center of rotation of the X-ray CT apparatus 100.

Figure 12A:
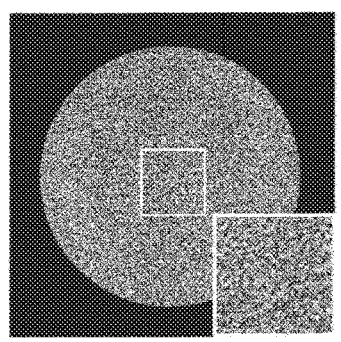
FIGS. 12A to 12C are explanatory views for explaining the results of the example of the first embodiment.
Figure 12B:
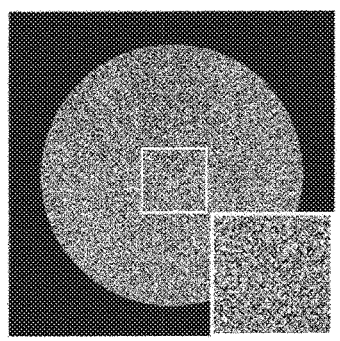
Figure 12C:
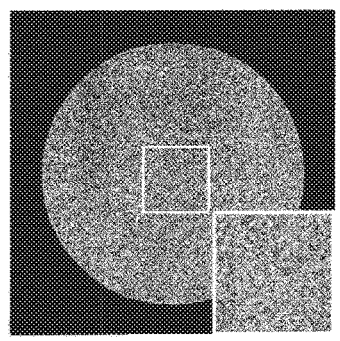

(a) of FIG. 12 illustrates an initial image 611, (b) of FIG. 12 illustrates a CT image 612 obtained by iteratively correcting the initial image 611 by a method in the related art, and (c) of FIG. 12 illustrates a CT image 613 obtained by iteratively correcting the initial image 611 by the method of the present embodiment. Here, the method in the related art is an iterative correction using the same iterative correction parameter $\beta$ regardless of the pixel position j. The method of the present embodiment is an iterative correction using the optimal iterative correction parameter $\beta_I$ (j) for each pixel position j. The white frame below the right side of each image in (a) to (c) of FIG. 12 is the enlargement of the center portion of each reconstructed image. The window level (hereinafter referred to as "WL") was set to 0 [HU] and the window width (hereinafter referred to as "WW") was set to 100 [HU].

For the iterative correction, OS-SPS using a known subset method was used to set the number of times of repetition (iteration) to 60 and the number of subsets to 24. A constant value was set for the weight conditions set in the weight setting area 430 in FIG. 3, and 20% was set as a desired noise reduction rate for the desired imaging/image conditions.

It may be seen that the CT image 612 obtained by the method in the related art has an increased noise as compared with the initial image 611. In the meantime, it may be seen that the CT image 613 obtained by the method of this embodiment has a decreased noise as compared with the initial image 611. In the CT image 613 obtained by the method of the present embodiment, as a result of measuring a noise within the ROI set at the center thereof, the noise was reduced by about 20% from the initial image 611. That is, a noise reduction rate of 20% was achieved.

In this manner, it was revealed that a CT image achieving a desired noise reduction rate may be acquired by the method of this embodiment.

Second Embodiment

Next, a second embodiment of the present invention will be described. In the first embodiment, the reconstruction filter differs between the imaging conditions (actual imaging conditions) set by the user and the representative imaging conditions. In the meantime, in the second embodiment, the correction method for the measured projection data differs between the imaging conditions (actual imaging conditions) set by the user and the representative imaging conditions.

The X-ray CT apparatus of the second embodiment basically has the same configuration as the X-ray CT apparatus 100 of the first embodiment. However, as described above, the imaging conditions differ between the actual imaging conditions and the representative imaging conditions. Therefore, in the second embodiment, the process of the representative noise reduction rate converting unit 321 of the parameter determining unit 320 is different from that of the first embodiment. Hereinafter, the second embodiment will be described focusing on configurations different from those of the first embodiment.

The representative noise reduction rate converting unit 321 of the parameter determining unit 320 of the second embodiment will be described with reference to FIG. 13.

As in the first embodiment, the representative noise reduction rate converting unit 321 of the parameter determining unit 320 of the second embodiment converts the noise reduction rate designated in the actual imaging conditions into the representative noise reduction rate to be input to the table of the representative imaging conditions.

However, in the second embodiment, in place of the filter noise table 520 of the first embodiment, a correction method noise table for storing the noise increase/decrease ratio with respect to the reference correction method is further provided for each correction method. Then, the representative noise reduction rate converting unit 321 refers to the correction method noise table to convert the desired reduction rate (actual reduction rate) into the representative reduction rate (step S3201).

An example of the correction method noise table 540 of the second embodiment is illustrated in FIG. 14. As illustrated in the figure, the correction method noise table 540 stores the noise increase/decrease ratio 542 with respect to the reference correction method for each correction method 541 of the measured projection data.

As illustrated in FIG. 3 of the first embodiment, the correction method is classified as large, medium and small according to the effect and a designation is received according to the classification. Therefore, as for the correction method noise table 540, this classification (correction small, correction medium, correction large) is stored as the correction method 541.

The noise increase/decrease ratio 542 is calculated from SD measured on a representative phantom CT image acquired by using each projection data correction means of the correction effect small, medium and large. The correction method noise table 540 illustrated in this figure stores the noise increase/decrease ratio when a value of the correction effect small is 1.0.

For example, as a noise increase/decrease ratio in the case where the projection data correction means used for the imaging conditions has the correction effect small and the projection data correction means used as the representative imaging conditions has the correction effect medium, 0.77 (=0.77/1.0) may be obtained from the correction method noise table 540.

The correction method noise table 540 is created in advance and is held in the HDD device 134 or the like.

The representative noise reduction rate converting unit 321 uses the noise increase/decrease ratio to convert the actual noise reduction rate into the representative noise reduction rate according to the equation (8) in the same manner as in the first embodiment.

For example, when the correction effects of the actual imaging conditions and the representative imaging condition are small and medium, respectively, and the actual noise reduction rate is 75%, the representative noise reduction rate of the second embodiment is calculated as 67.5%=(1−(1−0.75)/0.77)×100) from the equation (8).

Since the other processes are the same as those in the first embodiment, the description thereof will not be repeated here.

As described above, as in the first embodiment, the X-ray CT apparatus 100 of the second embodiment includes the X-ray generating unit 121, the X-ray detecting unit 122, and the image generating unit 130 including the iterative reconstructing unit 233. The iterative reconstructing unit 233 includes the table unit 310, the parameter determining unit 320, and the iterative correcting unit 330. The parameter determining unit 320 may include the representative noise reduction rate converting unit 321, the calculation table referring unit 322, the weight calculating unit 323, and the parameter converting unit 324. The table unit 310 may further include the reference weight calculating unit 312.

In addition, the correction method for the measured projection data differs between the imaging conditions set by the user and the representative imaging conditions, the iterative reconstructing unit 233 may further include the correction method noise table 30 that stores the noise increase/decrease ratio with respect to the reference correction method for each correction method, and the representative noise reduction rate converting unit 321 may refer to the correction method noise table 540 to convert the desired reduction rate into the representative reduction rate.

In this manner, according to the second embodiment, even when the correction method of the measured projection data of the actual imaging conditions is different from that of the representative imaging conditions, a CT image may be acquired that achieves a desired noise reduction rate.

That is, according to the second embodiment, even when the actual imaging conditions are different from the representative imaging conditions, as in the first embodiment, the reduction rate of the actual imaging conditions is converted into the reduction rate of the representative imaging conditions to obtain the optimal iterative correction parameter. Therefore, similarly to the first embodiment, the optimal iterative correction parameter in the actual imaging conditions may be obtained without increasing the number of man-days and the number of tables required for table creation.

Further, similarly to the first embodiment, each pixel may be iteratively correct using the optimal iterative correction parameter $\beta_I(j)$. Therefore, a high-quality CT image may be obtained that implements a desired noise reduction rate.

Further, according to the second embodiment, the noise increase/decrease ratio is acquired using the correction method noise table 540 without calculating the noise (SD) of the actual imaging conditions. However, the present invention is not limited thereto. Even in the present embodiment, similarly to the first embodiment, a CT image may be acquired using the correction means of each of the actual imaging conditions and the representative imaging conditions, the SD of the predetermined region (ROI) may be measured, and a result of the measurement may be used to calculate the noise increase/decrease ratio.

Figure 15A:
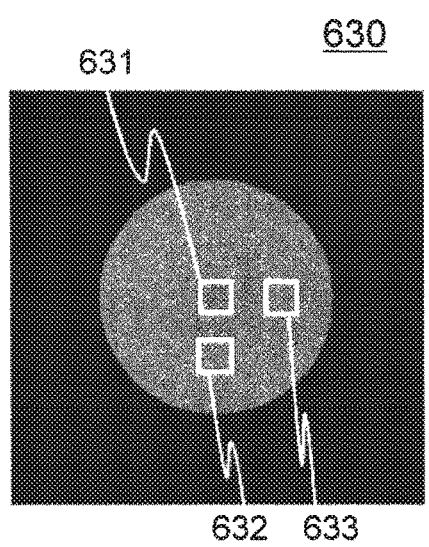
FIGS. 15A and 15B are explanatory views for explaining a noise increase/decrease ratio calculation method of the second embodiment.
Figure 15B:
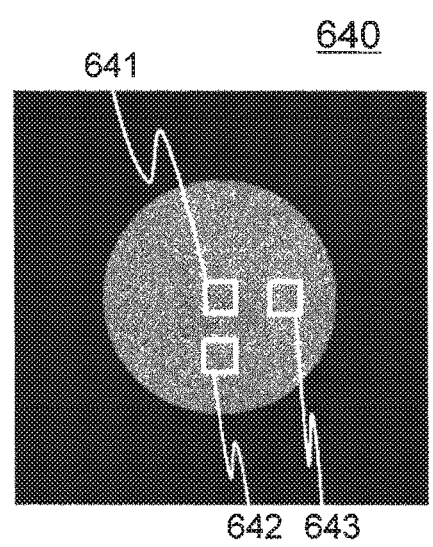

(a) and (b) of FIG. 15 illustrate CT images 630 and 640 obtained from the result of correcting the measured projection data using the correcting means designated by the actual imaging conditions and the representative imaging conditions, respectively. The phantom-centered ROIs 631 and 641 are areas used for SD measurement. The noise increase/decrease ratio is calculated from this measurement result according to the equation (5).

The area used for the SD measurement is not limited to the phantom-centered areas 621 and 631. For example, the area used for the SD measurement may be areas 630 and 640 at the same position of the images 630 and 640, for example, the surrounding areas 632 and 642 and the surrounding areas 633 and 643.

Further, it is unnecessary to uniformly set the noise increase/decrease ratio in each image. The noise increase/decrease ratio may be obtained independently for each position. That is, in the above example, the noise increase/decrease ratio in the areas 631 and 641, the noise increase/decrease ratio in the areas 632 and 642, and the noise increase/decrease ratio in the areas 633 and 643 may be calculated respectively.

Furthermore, even in the second embodiment, as in the first embodiment, the CT reconstruction method may be, for example, a known half reconstruction or a reconstruction using the measured projection data of one round of 360 degrees or more.

Third Embodiment

A third embodiment of the present invention will be described. In the first embodiment, the reconstruction filter differs between the imaging conditions (actual imaging conditions) set by the user and the representative imaging conditions. In the meantime, in the third embodiment, the range of the measured projection data used to generate a CT image and the range of the measured projection data used for the iterative correction differ between the imaging conditions (actual imaging conditions) set by the user and the representative imaging conditions.

The X-ray CT apparatus of the third embodiment basically has the same configuration as the X-ray CT apparatus 100 of the first embodiment. However, as described above, the imaging conditions differ between the actual imaging conditions and the representative imaging conditions. Therefore, in the third embodiment, the process of the representative noise reduction rate converting unit 321 of the parameter determining unit 320 is different from that of the first embodiment. Hereinafter, the third embodiment will be described focusing on configurations different from those of the first embodiment.

The representative noise reduction rate converting unit 321 of the parameter determining unit 320 of the third embodiment will be described with reference to FIG. 16.

Even in the third embodiment, as in the first embodiment, the representative noise reduction rate converting unit 321 of the parameter determining unit 320 converts the noise reduction rate designated in the actual imaging conditions into the representative noise reduction rate to be input to the table of the representative imaging conditions. However, in the third embodiment, as in the first embodiment, the filter noise table 520 is not provided.

That is, the representative noise reduction rate converting unit 321 of the third embodiment uses the measured projection data range used to generate the CT image in each of the actual imaging conditions and the representative imaging conditions to convert the desired reduction rate into the representative reduction rate (step S4201).

Here, the measured projection data range refers to a range of measured projection data used for generation of an initial image and reconstruction by iterative correction, as described above, and is specified by a projection angle.

Assuming that the SD of the CT image obtained when the projection data range is designated as 360 degrees is 1, the SD of the CT image obtained when the projection data is designated as an ANG degree is expressed by the following equation (17).

$$SD=\sqrt{(360/ANG)} \qquad (17)$$

For example, when the weights that are ratios at which data are used in the projection angle direction, the channel direction of the detection elements or the direction of the slice column of the detection elements are equal for the range of all the projection data, the SD of the CT image obtained when the projection data range is designated as 180 degrees is increased by √2 times, and the SD of the CT image obtained when the projection data range is designated as 270 degrees is increased by 1.15 times. In the meantime, when the weights which are ratios at which the data are used in each direction is changed for the range of the projection data of the CT image, it is necessary to calculate the amount of increase of the SD in consideration of the weights.

The representative noise reduction rate converting unit 321 calculates the noise increase/decrease ratio using the following equation (18).

[Equation 18]

$$\text{Noise increase/decrease ratio} = \frac{\text{Initial projection data range of representative imaging conditions}}{\text{Initial projection data range of actual imaging conditions}} \times \frac{\text{Iterative-corrected projection data range of actual imaging conditions}}{\text{Iterative-corrected projection data range of representative imaging conditions}} \quad (18)$$

The initial projection data range is a measured projection data range at the time of initial image generation and the iterative-corrected projection data range is a measured projection data range used for the iterative correction. In a helical scan, since the range of the measured projection data collected at each pixel position of the CT image is changed, the noise increase/decrease ratio at the center position of the CT image may be calculated as a representative value or the noise increase/decrease ratio at each pixel position may be calculated.

For example, in the actual imaging conditions, the measured projection data range used to generate the initial image is set to 180 degrees and the measured projection data range used for the iterative correction is set to 360 degrees. In the representative imaging conditions, the measured projection data range used to generate the initial image is set to 360 degrees and the measured projection data range used for the iterative correction is set to 360 degrees. In this case, the noise increase/decrease ratio calculated by the equation (18) is 1/√2 (=(1/√2)×(1/1)).

The representative noise reduction rate converting unit 321 uses this noise increase/decrease ratio to convert the actual noise reduction rate into the representative noise reduction rate according to the equation (8) in the same manner as in the first embodiment.

That is, the representative noise reduction rate converting unit 321 of the third embodiment calculates the ratio of the initial projection data range of the representative imaging conditions to the initial projection data range used for the actual imaging conditions and the ratio of the iterative-corrected projection data range of the actual imaging conditions to the iterative-corrected projection data range of the representative imaging conditions, and multiplies these ratios to obtain a noise reduction rate. Then, the obtained noise reduction rate is used to calculate a noise of the initial image of the representative imaging conditions and a noise (target noise) of the iterative-corrected CT image of the actual imaging conditions.

At this time, the representative noise reduction rate converting unit 321 may be configured to contribute to the weights which are ratios at which data are used in the projection angle direction, the channel direction of the detection elements or the direction of the slice column of the detection elements, for the projection data range of the CT image.

The other processes are the same as those in the first embodiment and therefore, the description thereof will not be repeated here.

As described above, the X-ray CT apparatus 100 of the third embodiment includes the X-ray generating unit 121, the X-ray detecting unit 122, and the image generating unit 130 including the iterative reconstructing unit 233. The iterative reconstructing unit 233 includes the table unit 310, the parameter determining unit 320, and the iterative correcting unit 330. The parameter determining unit 320 may include the representative noise reduction rate converting unit 321, the calculation table referring unit 322, the weight calculating unit 323, and the parameter converting unit 324. The table unit 310 may further include the reference weight calculating unit 312.

The measured projection data range used to generate the CT image and the measured projection data range used for the iterative correction differ between the imaging conditions set by the user and the representative imaging conditions. The representative noise reduction rate converting unit 321 may use the measured projection data range used to generate the CT image in each of the imaging conditions set by the user and the representative imaging conditions and the measured projection data range used for the iterative correction to convert the desired reduction rate into the representative reduction rate.

In this manner, according to the third embodiment, even when the projection data range different from the representative imaging conditions is used as the actual imaging conditions, a CT image may be acquired that achieves a desired noise reduction rate.

That is, according to the third embodiment, even when the actual imaging conditions are different from the representative imaging conditions, as in the first embodiment, the reduction rate of the actual imaging conditions is converted into the reduction rate of the representative imaging conditions to obtain the optimal iterative correction parameter. Therefore, similarly to the first embodiment, the optimal iterative correction parameter in the actual imaging conditions may be obtained without increasing the number of man-days and the number of tables required for table creation.

Further, similarly to the first embodiment, each pixel may be iteratively corrected by using the optimal iterative correction parameter $\beta_I(j)$. Therefore, a high-quality CT image may be obtained that implements a desired noise reduction rate.

In the third embodiment, the noise increase/decrease ratio is calculated according to the above equation (18). However, the present invention is not limited to this method. For example, a table corresponding to a combination of measured projection data ranges to be used may be created in advance and referred to.

When weights contributing to reverse projection are changed for each projection angle as in a known weighted analytical reconstruction, it is necessary to calculate the relative increase/decrease ratio of SD from the weight of each projection angle in the same way. In this case, it is necessary to calculate the relative increase/decrease ratio of SD in the same way when changing the weight not only in the direction of the projection angle but also in the channel direction or the slice direction.

Fourth Embodiment

Next, a fourth embodiment of the present invention will be described. In each of the earlier-described embodiments, it is assumed that the noises at the convergence stage of the iterative correction are the same. In practice, however, depending on the set iteration times, the noises may not reach the convergence stage. Therefore, in the third embodiment, the number of the iteration times is predetermined in advance, and in the case where the initial image obtained in the actual imaging conditions does not reach the noises in the convergence stages with the number of the repetition (iteration) times, it is notified to the user before the iterative correction process.

The X-ray CT apparatus of the third embodiment basically has the same configuration as the X-ray CT apparatus 100 of the first embodiment. However, since it is necessary to notify the user as described above, as illustrated in FIG. 17, the iterative reconstructing unit 233 of the third embodiment further includes a propriety discriminating unit 341 and a discrimination result notifying unit 342.

[Propriety Discriminating Unit]

The propriety discriminating unit 341 discriminates the propriety of the CT image (initial image) generated from the measured projection data obtained according to the actual imaging conditions. When discriminating that the CT image (initial image) does not converge within the predetermined number of time of repetition in the iterative correction, the propriety discriminating unit 341 discriminates that the CT image is inappropriate. That is, it is discriminated whether or not the given initial image is an initial image that may be corrected iteratively by the method of each of the above embodiments, and if not, the user is notified of that effect.

The discrimination is made according to the actual noise reduction rate obtained from the noise of the given initial image and the noise of the convergence stage (hereinafter, referred to as a convergence noise). That is, when the actual noise reduction rate does not become the convergence noise with a predetermined number of times, the propriety discriminating unit 341 discriminates that the CT image is inappropriate.

The propriety discriminating unit 341 discriminates the propriety based on a predetermined reduction rate threshold value. The threshold value used as a criterion for determination is preset according to the number of times of iteration. The set threshold value is the upper limit value (maximum threshold value TH %) and the lower limit value (minimum threshold value TL %) of the noise reduction rate at which the noise of the initial image becomes a noise at the convergence stage with a predetermined number of times.

When the initial image is actually given, the propriety discriminating unit 341 calculates the noise reduction rate (A %) from the noise of the initial image and the noise of the convergence stage. Then, the propriety discriminating unit 341 discriminates whether or not the calculated noise reduction rate is between the maximum threshold value TH and the minimum threshold value TL, and when the calculated noise reduction rate is not between the two threshold values, the user is notified of that effect. That is, when TL≤A≤TH, it is discriminated that the initial image may be processed, and when A<TL or A>TH, it is discriminated that the initial image may not be processed.

For example, as illustrated in (a) of FIG. 6, the threshold values (TH and TL) used for the discrimination are obtained from the result of iterative correction by using a representative phantom in advance and using a plurality of different reference parameters βb.

In more detail, FIG. 18 is a graph 552 showing a change in noise when the representative iterative correction parameter is used. The horizontal axis represents the number of times of repetition (iteration) and the vertical axis represents noise. The number of times of repetition (iteration) of 0 means an initial image. In the graph 552, the convergence stage is such that the SD does not fluctuate when the number of times of repetition (iteration) is 60 or more. The convergence noise is 554.

At this time, when the noise reduction rate A % calculated from the noise 553 of the given initial image and the convergence noise 554 is larger than the maximum threshold value TH %, it does not reach the noise of the convergence stage with the number of times of repetition (iteration) of 60. The propriety discriminating unit 341 of the fourth embodiment compares A % with TH % and discriminates to be inappropriate when the noise reduction rate is larger than the predetermined maximum threshold TH %.

For example, since the graph 555 uses an initial image whose noise reduction rate B % is equal to or larger than the maximum threshold value TH %, it does not reach the convergence noise 554 with the number of times of repetition (iteration) of 60.

On the contrary, when the noise of the initial image is 556, even when the noise reduction rate C % determined from the noise 556 and the convergence noise 554 is equal to or less than the minimum threshold value TL %, it does not reach the convergence noise 554 with the number of times of repetition (iteration) of 60. Even in this case, the propriety discriminating unit 341 discriminates to be inappropriate.

[Discrimination Result Notifying Unit]

The discrimination result notifying unit 342 notifies the user when the result of the discrimination by the propriety discriminating unit 341 is inappropriate. The notification to the user is displayed, for example, by an error message or the like. However, the present invention is not limited thereto. For example, the user may be notified by performing a process such as stopping the operation, instead of output by display or the like.

Furthermore, the user may be notified so as to change the initial image to an initial image that converges into a threshold value, or it may be configured to be automatically changed.

For example, when it is configured to automatically changed, the iterative reconstructing unit 233 includes an image changing unit 343 in addition to the determination result notifying unit 342 or in place of the determination result notifying unit 342.

The image changing unit 343 changes the CT image (initial image) when the determination result by the propriety determining unit 341 is inappropriate. At this time, the image changing unit 343 changes the CT image (initial image) to a CT image whose reduction rate is within a threshold value and is closest to the reduction rate of the CT image (initial image) to be discriminated. That is, the initial image to be changed is an initial image whose noise reduction rate converges into the threshold value and is closest to the noise of the initial image.

In the fourth embodiment, a case where the threshold value is held for one type of repetition (iteration) times of 60 has been described. However, the present invention is not limited thereto. For example, the threshold value may be held for plural types of the number of repetition (iteration) times of, for example, 100, 200, and the like.

As described above, similarly to the first embodiment, the X-ray CT apparatus 100 of the fourth embodiment includes the X-ray generating unit 121, the X-ray detecting unit 122, and the image generating unit 130 including the iterative reconstructing unit 233. The iterative reconstructing unit 233 includes the table unit 310, the parameter determining unit 320, and the iterative correcting unit 330. The parameter determining unit 320 may include the representative noise reduction rate converting unit 321, the calculation table referring unit 322, the weight calculating unit 323, and the parameter converting unit 324. The table unit 310 may further include the reference weight calculating unit 312.

The iterative reconstructing unit 233 further includes the propriety discriminating unit 341 that discriminates the propriety of the CT image generated from the measured projection data. In the iterative correction, when the propriety discriminating unit 341 discriminates that the CT image does not converge into the predetermined number of times of repetition, it may be discriminated that the CT image is inappropriate. In addition, the iterative reconstructing unit 233 may include at least one of the discrimination result notifying unit 342 for notifying the user when the discrimination result by the propriety discriminating unit 341 is inappropriate and the image changing unit 343 for changing the CT image when the discrimination result by the propriety discriminating unit 341 is inappropriate.

In this manner, according to the fourth embodiment, when the initial image obtained in the actual imaging conditions does not reach the noise at the convergence stage with the predetermined number of times of iteration, this is notified to the user. Then, the user may change the imaging conditions and the like to change the initial image such that it reaches the noise of the convergence stage with the predetermined number of times of iteration. Alternatively, the initial image may be automatically changed such that it reaches the noise of the convergence stage with the predetermined number of times of iteration.

Therefore, according to the fourth embodiment, when using the method described in the first to third embodiments, the initial image always satisfies the necessary conditions. Therefore, according to the fourth embodiment, a high-quality CT image may be obtained that reliably achieves a desired noise reduction rate.

In particular, when the image changing unit 343 is provided, by performing the iterative correction using an image having a noise close to the initial image obtained in the actual imaging conditions, an image having image quality close to the image quality of the initial image of the actual imaging conditions and having a desired reduction rate may be acquired.

<Modification of Weight Conditions>

In each of the above embodiments, the case where the weights of all the detection elements are made constant has been described by way of example. However, the present invention is not limited thereto. For example, a weight corresponding to the number of photons detected by a detection element may be used through the weight setting area 430.

In this case, since the weighting conditions are different, the processes of the reference weight calculating unit 312, the weight calculating unit 323, and the parameter converting unit 324 are different.

[Reference Weight Calculating Unit]

In each of the above embodiments, since the weight of each detection element is made constant, the weight image is calculated as $W_I(j)$. However, in the present modification, the weight of each detection element is set according to the number of photons. It is assumed that the weight of each detection element i is $W_P(i)$.

The reference weight calculating unit 312 of this modification performs the same process as the CT image reconstruction on the weight $W_P(i)$ of each detection element i, as in the above embodiments, to obtain a weight $W_{IP}(j)$ of each pixel position in the reference area. Then, as in the above embodiments, the values such as the average value, the maximum value, the minimum value, etc. obtained from each weight value are set as the reference weight Wb. Here, j represents a pixel position.

[Weight Calculating Unit]

The weight calculating unit 323 of the present modification performs the same process as the CT image reconstruction on the weight $W_P(i)$ of each detection element as in the above embodiments, to obtain a weight image $W_{IP}(j)$.

[Parameter Converting Unit]

The parameter converting unit 324 of the present modification uses the reference parameter $\beta_b$ calculated by the same method as in each of the above embodiments, the reference weight $W_b$ calculated by the method of the present modification and the weight value $W_{IP}(j)$ of each pixel position to calculate an iterative correction parameter distribution $\beta_{IP}(j)$ of the present modification according to the following equation (19).

[Equation 19]

$$\beta_{IP}(j) = \beta_b \cdot \frac{W_{IP}(j)}{W_b} \quad (19)$$

In addition, the iterative correcting unit 330 performs the iterative correction using the calculated iterative correction parameter $\beta_{IP}(j)$ of each pixel position j. Details of the iterative correction process are the same as those in the above embodiments.

FIG. 19 illustrates a weight image $W_{IP}(j)$ 620 calculated using the number of photons of a detection element from a result of imaging a cylindrical phantom having a diameter of 30 cm and a height of 100 cm and filled with water. The phantom was placed at a position moved by 10 cm downward from the rotation center. As illustrated in this figure, the weight images $W_{IP}(j1)$ and $W_{IP}(j2)$ of the respective positions j1 and j2 have different values.

In this manner, even when the number of photons of a detection element is set as the weight conditions, by using the weight value (the parameter $\beta$ image $\beta_{IP}(j)$ at each position) for each position (pixel) as a weight at the time of the iterative correction, a CT image may be acquired that achieves a desired noise reduction rate.

<Other Modifications>

The above first to fourth embodiments may be used in combination. Even when the actual imaging conditions are different from the representative imaging conditions and the plurality of conditions by the combination, the desired noise reduction rate of the actual imaging conditions may be converted into the target noise reduction rate of the representative imaging conditions to implement a desired noise reduction rate with a simple configuration.

In the first to third embodiments, the reconstruction filter, the correction method for the measured projection data, and the measured projection data range have been described as the imaging conditions different from the actual imaging conditions. However, the different imaging conditions are not limited thereto. Any imaging conditions may be dealt with as long as they are capable of grasping the amount of change in noise caused by changing the imaging conditions.

Further, in each of the above-described embodiments and modifications, in order to shorten the calculation time, a case where the processes of the table unit 310 and the parameter determining unit 320 are performed in advance has been described by way of example. However, the processes by the table unit 310 and the parameter determining unit 320 are not necessarily performed in advance. These processes may be performed at the time of imaging or at the time of generating an image according to the imaging conditions or the reconstruction conditions designated by the user before the process by the iterative correcting unit 330.

Further, for example, the weight calculating unit 323 and the parameter converting unit 324 may be added as parts of the Prior calculating unit 335. At this time, the weight image $W_I$ (j) illustrated in the equation (9) is equivalent to the following item 20 which is a portion other than P2 in the denominator of the right side of the equation (15).

[Equation 20]

$$\sum_{i=1}^{I} W(i)C(i, j) \sum_{l=1}^{L} C(i, l) \quad (20)$$

Therefore, by substituting $\beta_I$ (j) of the equation (9) into $\beta$ of the equation (15) (the equations (13) and (14)), the weight calculating unit 323 and the parameter converting unit 324 may be excluded from the Prior calculating unit 335. As a result, the amount of calculation required for redundant weight calculation of $W_I$ (j) may be reduced.

In each of the above-described embodiments and modifications, the input unit 110 and the image generating unit 130 are not necessarily integrated with the main body apparatus (X-ray CT apparatus 100) including the imaging unit 120 and may be built on an information processing apparatus independent of the imaging unit 120. In this case, the information processing apparatus and the X-ray CT apparatus 100 may be interconnected via a network. Further, only the image generating unit 130 may be built, as a processing device for processing the measured projection data, on the independent information processing apparatus.

In this case, the X-ray CT apparatus 100 is configured to be able to transmit the iterative-corrected CT image to an external terminal via a network such as an LAN, a telephone line or the Internet using a network adapter.

In each of the above-described embodiments and modifications, $\beta$ ($\beta_I$(j)) which is a coefficient of a smoothing term is used as the iterative correction parameter for controlling the image quality. However, the present invention is not limited thereto. The iterative correction parameter may use a coefficient of Likelihood calculation or two coefficients of calculation as long as it is a parameter that determines the ratio between the Likelihood calculation and the Prior calculation.

The iterative reconstruction method illustrated by the above equation (10) is a non-limiting example. Other methods such as OS-SPS, OS-SPS-TV, PWLS, OS-PWLS, ASIRT, MSIRT, GRADY, CONGR, ART, SART, SART-TV, OS-SART, OS-SART-TV, ML-EM, OS-EM, FIRA, RAMLA, and DRAMA known in the art may be used.

Further, in each of the above-described embodiments and modifications, the case where the measured projection data is acquired by the scan method in the related art in which the bed 125 and the gantry 123 are in a stationary state has been described by way of example, but the present invention is not limited thereto. For example, the measured projection data may be acquired by a step-and-shoot method in which the scanning in the related art is performed while repeating the operation and stop of the bed 125 at regular intervals or in a helical scan method in which the bed 125 is imaged while being moved.

Furthermore, in each of the above-described embodiments and modifications, the X-ray CT apparatus 100 for a living body has been described by way of example. However, the present invention may be applied to an X-ray CT apparatus for non-destructive inspection such as explosive inspection and product inspection.

Moreover, in each of the above-described embodiments and modifications, the third-generation multi-slice X-ray CT apparatus 100 known in the art has been described by way of example. However, the X-ray CT apparatus may be the first, second, and fourth-generation X-ray CT apparatus known in the art or may be a single-slice X-ray CT apparatus or electron beam CT known in the art.

EXPLANATION OF REFERENCE NUMERALS

100: X-ray CT apparatus, 101: subject, 110: input unit, 111: keyboard, 112: mouse, 113: memory, 114: CPU, 115: HDD device, 116: data bus, 132: memory, 120: imaging unit, 133: CPU, 121: X-ray generating unit, 122: X-ray detecting unit, 123: gantry, 124: rotating plate, 125: bed, 126: opening, 127: gantry controller, 128: X-ray controller, 129: bed controller, 130: image generating unit, 131: DAS, 132: memory, 133: CPU, 134: HDD device, 135: monitor, 136: data bus, 211: imaging condition input unit, 221: imaging control unit, 222: signal acquiring unit, 231: signal collecting unit, 232: correction processing unit, 233: iterative reconstructing unit, 234: image display unit, 310: table unit, 311: table calculating unit, 312: reference weight calculating unit, 313: calculation table storage unit, 320: parameter determining unit, 321: representative noise reduction rate converting unit, 322: calculation table referring unit, 323: weight calculating unit, 324: parameter converting unit, 330: iterative correcting unit, 331: analytical reconstructing unit, 332: forward projecting unit, 333: differentiating unit, 334: reverse projection processing unit, 335: Prior calculating unit, 336: image correcting unit, 400: imaging condition reception screen, 410: X-ray condition setting area, 420: reconstruction range setting area, 430: weight setting area, 440: imaging portion setting area, 450: imaging/image setting area, 460: reconstruction filter setting area, 470: projection data correction setting area, 480: projection data range setting area, 510: CT image, 511: ROI, 512: measured value, 513: approximate curve, 514: ROI, 520: filter noise table, 521: type of reconfiguration filter, 531: noise, 532: noise of initial image by the actual imaging conditions, 533: noise of initial image by the representative imaging conditions, 534: noise convergence value, 540: correction method noise table, 541: correction method of the measured projection data, 542: noise increase/decrease ratio, 552: noise change graph, 553: noise of initial image, 554: convergence noise, 555: noise change graph, 556: noise of initial image, 611: initial image, 612: CT image, 613: CT image, 620: weight image, 630: CT image, 631: area, 632: area, 633: area, 640: CT image, 641: area, 642: area, 643: area, 710: parameter table, 711: the number of times of iteration, 712: reconfiguration filter, 713: table

The invention claimed is:

1. An X-ray CT apparatus comprising:
an X-ray generating unit that generates an X-ray according to set imaging conditions;
an X-ray detecting unit that detects the X-ray transmitted through a subject with a plurality of detection elements to obtain measured projection data; and
an image generating unit including an iterative reconstructing unit that performs iterative correction on a CT image so that calculated projection data obtained by forward projection calculation from the CT image generated from the measured projection data becomes equal to the measured projection data,
wherein the iterative reconstructing unit includes:
a table unit that stores, as a table, the relationship between a reduction rate which is a rate at which a noise or an X-ray dose is reduced by the iterative correction for the CT image acquired under representative imaging conditions and a reference parameter which is a parameter used for the iterative correction for implementing the reduction rate;
a parameter determining unit that converts the reduction rate desired in the actual imaging conditions, which are the imaging conditions at the time of actual imaging, into a representative reduction rate which is a reduction rate in the representative imaging conditions, and refers to the table to determine an iterative correction parameter to implement the desired reduction rate; and
an iterative correcting unit that performs the iterative correction using the iterative correction parameter determined by the parameter determining unit.

2. The X-ray CT apparatus according to claim 1, wherein the parameter determining unit includes:
a representative noise reduction rate converting unit that uses a noise increase/decrease ratio which is a ratio of noise of the CT image acquired in the representative imaging conditions to noise of the CT image acquired in the actual imaging conditions due to a difference between the representative imaging conditions and the actual imaging conditions to convert the desired reduction rate into the representative reduction rate;
a calculation table referring unit that extracts a reference parameter corresponding to the converted representative reduction rate from the table;
a weight calculating unit that calculates a weight for each pixel on the CT image based on the weight of each detection element; and
a parameter converting unit that determines an iterative correction parameter for each pixel from the weight for each pixel and the reference parameter.

3. The X-ray CT apparatus according to claim 2, further comprising a reference weight calculating unit that calculates a weight value of a pixel in an area serving as a predetermined reference on the CT image, as a reference weight, based on the weight of each detection element,
wherein the parameter converting unit further uses the reference weight to determine an iterative correction parameter for each pixel.

4. The X-ray CT apparatus according to claim 2, wherein reconstruction filters differ between the imaging conditions set by a user and the representative imaging conditions,
the iterative reconstructing unit further includes a filter noise table that stores a noise of the CT image when the same subject is imaged under the representative imaging conditions for each of the reconstruction filters, and the representative noise reduction rate converting unit refers to the filter noise table to convert the desired reduction rate into the representative reduction rate.

5. The X-ray CT apparatus according to claim 2, wherein correction methods differ between the imaging conditions set by a user and the representative imaging conditions,
the iterative reconstructing unit further includes a correction method noise table that stores a noise increase/decrease ratio with respect to a reference correction method for each of the correction methods, and
the representative noise reduction rate converting unit refers to the correction method noise table to convert the desired reduction rate into the representative reduction rate.

6. The X-ray CT apparatus according to claim 2, wherein a measured projection data range used to generate the CT image and a measured projection data range used for the iterative correction differ between the imaging conditions set by a user and the representative imaging conditions, and
the representative noise reduction rate converting unit uses the measured projection data range used to generate the CT image and the measured projection data range used for the iterative correction in each of the imaging conditions set by the user and the representative imaging conditions to convert the desired reduction rate into the representative reduction rate.

7. The X-ray CT apparatus according to claim 1, wherein the iterative reconstructing unit further includes a propriety discriminating unit that discriminates the propriety of the CT image generated from the measured projection data, and
the propriety discriminating unit discriminates that the CT image is inappropriate when it is discriminated that the CT image does not converge within a predetermined number of times of repetition in the iterative correction.

8. The X-ray CT apparatus according to claim 7, wherein the iterative reconstructing unit further includes at least one of a discrimination result notifying unit that notifies the user when a result of the discrimination by the propriety discriminating unit is inappropriate and an image changing unit that changes the CT image when the discrimination result by the propriety discriminating unit is inappropriate.

9. The X-ray CT apparatus according to claim 2, wherein the value of the weight for each detection element is either constant or a value proportional to the number of photons detected by each of the detection elements.

10. A method for determining an iterative correction parameter to be used for iterative correction in an X-ray CT apparatus including an X-ray generating unit that generates an X-ray according to set imaging conditions, an X-ray detecting unit that detects the X-ray transmitted through a subject with a plurality of detection elements to obtain measured projection data, and an image generating unit including an iterative reconstructing unit that performs iterative correction on the CT image so that calculated projection data obtained by forward projection calculation from the CT image generated from the measured projection data becomes equal to the measured projection data, the method comprising:
converting a reduction rate, which is a ratio at which a noise or an X-ray dose of the CT image by the iterative correction in actual imaging conditions is reduced, into the reduction rate in predetermined representative imaging conditions; and
referring to a pre-stored relationship between the reduction rate in the representative imaging conditions and a reference parameter, which is a parameter used for the iterative correction in order to implement the reduction rate, to determine an iterative correction parameter.

11. An X-ray CT apparatus comprising:

an X-ray generating unit that generates an X-ray according to set imaging conditions;

an X-ray detecting unit that detects the X-ray transmitted through a subject with a plurality of detection elements to obtain measured projection data; and an image generating unit including an iterative reconstructing unit that performs iterative correction so that calculated projection data obtained by forward projection calculation from a CT image generated from the measured projection data becomes equal to the measured projection data, wherein the iterative reconstructing unit includes:

a table unit that stores, as a table, a relationship between a reduction rate which is a ratio at which a noise or an X-ray dose is reduced by the iterative correction for the CT image acquired under representative imaging conditions and a reference parameter which is a parameter used for the iterative correction for implementing the reduction rate;

a parameter determining unit that converts the reduction rate desired in actual imaging conditions, which are the imaging conditions at the time of actual imaging, into the representative reduction rate which is a reduction rate in the representative imaging conditions, and refers to the table to determine the iterative correction parameter to implement the desired reduction rate; and an iterative correcting unit that performs the iterative correction using the iterative correction parameter determined by the parameter determining unit.

* * * * *